United States Patent
El-Araby et al.

(10) Patent No.: US 10,821,096 B1
(45) Date of Patent: *Nov. 3, 2020

(54) COMPOUNDS FOR INHIBITING NS3 AND COMPOSITIONS CONTAINING THE INHIBITED PROTEIN

(71) Applicant: King Abdulaziz University, Jeddah (SA)

(72) Inventors: Moustafa E. El-Araby, Jeddah (SA); Abdelsattar Mansour Omar, Jeddah (SA); Mahmoud Abdelkhalek El-Faky, Jeddah (SA); Sameh Hamdy Abdelmageed Soror, Jeddah (SA); Maan Talaat Khayat, Jeddah (SA); Hani Zakariah Asfour, Jeddah (SA); Faida Hassan Bamane, Jeddah (SA)

(73) Assignee: King Abdulaziz University, Jeddah (SA)

( * ) Notice: Subject to any disclaimer, the term of this patent is extended or adjusted under 35 U.S.C. 154(b) by 0 days.

This patent is subject to a terminal disclaimer.

(21) Appl. No.: 16/986,863

(22) Filed: Aug. 6, 2020

Related U.S. Application Data

(63) Continuation of application No. 16/384,472, filed on Apr. 15, 2019.

(51) Int. Cl.
| | |
|---|---|
| *A61K 31/4164* | (2006.01) |
| *A61K 31/55* | (2006.01) |
| *C07D 233/64* | (2006.01) |
| *C07D 233/54* | (2006.01) |
| *C07C 279/04* | (2006.01) |
| *C07C 279/10* | (2006.01) |
| *C07C 279/12* | (2006.01) |
| *C07D 279/16* | (2006.01) |
| *A61P 31/14* | (2006.01) |

(52) U.S. Cl.
CPC .......... *A61K 31/4164* (2013.01); *A61P 31/14* (2018.01)

(58) Field of Classification Search
CPC .. A61K 31/4164; A61K 31/55; C07D 233/64; C07D 233/54; C07C 279/04; C07C 279/10; C07C 279/12; C07C 279/16
USPC .......... 514/400, 565, 634; 548/341.5, 340.1; 564/230

See application file for complete search history.

(56) References Cited

U.S. PATENT DOCUMENTS

| | | |
|---|---|---|
| 6,599,926 B2 | 7/2003 | Pinto et al. |
| 2006/0258666 A1 | 11/2006 | Player et al. |
| 2007/0249649 A1 | 10/2007 | Illig et al. |

FOREIGN PATENT DOCUMENTS

| | | |
|---|---|---|
| EP | 1479674 A1 | 11/2004 |
| WO | WO97/31900 | 4/1997 |
| WO | WO 02/00647 A1 | 1/2002 |
| WO | WO 2006/047504 A1 | 5/2006 |
| WO | WO 2008/154271 A1 | 12/2008 |
| WO | WO 2012/143599 A1 | 10/2012 |
| WO | WO 2017/137319 A1 | 8/2017 |

OTHER PUBLICATIONS

Igumnova et al., "Synthesis and antimicrobial activity of small cationic amphipathic aminobenzamide marine natural product mimics and evaluation of relevance against clinical isolates including ESBL-CARBA producing multi-resistant bacteria" Bioorg. Med. Chem. 24 (2016), pp. 5884-5894. (Year: 2016).*
A.B. Voet, et al. "Prebiotic adenine synthesis from HCN—Evidence for a newly discovered major pathway" Bioorganic Chemistry, vol. 12, Issue 1, Sep. 1983, pp. 1-2 (Abstract Only).
A. Chittiboyina, et al. "Addition of lithioimidazoles to isocyanates followed by Pd-coupling: access to 4-substituted imidazole-2,5-dicarboxamides" Tetrahedron Letters, vol. 45, 2004, pp. 1869-1872.
Abutaleb, A., S. Kottilil and E. Wilson, "Glecaprevir/pibrentasvir expands reach while reducing cost and duration of hepatitis C virus therapy", Hepatol. Int. (2018), 12: pp. 214-222. (Year: 2018).
Zanetti, A., L. Romano and S. Bianchi, "Primary prevention of hepatitis C virus infection", Vaccine 21, (2003), pp. 692-695. (Year: 2003).
Igumnova et al., "Syn. and antimicrob. activ. of small cationic amphipathic aminobenzamide marine natural product mimics and evaluation of relevance against clinical isolates including ESBL-CARBA producing multi-resistant bacteria", Bioorg. Med. Chem. 24 (2016), pp. 5884-5894. (Year: 2016).

* cited by examiner

*Primary Examiner* — Matthew P Coughlin
*Assistant Examiner* — Sagar Patel
(74) *Attorney, Agent, or Firm* — Oblon, McClelland, Maier & Neustadt, L.L.P.

(57) ABSTRACT

Imidazole-based compounds as hepatitis C virus (HCV) inhibitors. The compounds have an imidazole core that is disubstituted via amide links. Also described are a pharmaceutical composition incorporating the imidazole-based compound, a method of preparing these compounds, and a method for using the pharmaceutical composition in the treatment of HCV infection.

5 Claims, 5 Drawing Sheets

COMPOUNDS FOR INHIBITING NS3 AND COMPOSITIONS CONTAINING THE INHIBITED PROTEIN

CROSS-REFERENCE TO RELATED APPLICATIONS

The present application is a Continuation of Ser. No. 16/384,472, having a filing date of Apr. 15, 2019.

STATEMENT OF FUNDING ACKNOWLEDGEMENT

This project was funded by the National Plan for Science, Technology and Innovation (MAARIFAH), King Abdulaziz City for Science and Technology, the Kingdom of Saudi Arabia under award number 12-BIO3193-03. The project was also supported by the Science and Technology Unit of King Abdulaziz University.

BACKGROUND OF THE INVENTION

Technical Field

The present disclosure relates to a family of disubstituted imidazole compounds. A pharmaceutical composition involving the compounds, a method of preparing the compounds, and a method of treating or inhibiting hepatitis C infection via inhibiting the functioning of the NS3 protease using the compounds are disclosed.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Hepatitis C is a life-threatening viral infection that is wide spread in the world [Organization, W. H., Global hepatitis report 2017. 2017]. Initially, the virus infects liver cells but remains asymptomatic for an extended period [Dickson, R. C., Clinical manifestations of hepatitis C. *Clinics in liver disease* 1997, 1 (3), 569-85]. This is an epidemiological challenge because patients diagnosed with hepatitis C come from two pools; recently-infected and later-stage asymptomatic. The initial symptoms of hepatitis C such as fever, fatigue, nausea, and liver tenderness can be misleading because they are tolerated by most patients. After several years of infection, the virus activates, replicates, and causes complications that start with liver scarring, fibrosis followed by cirrhosis and eventually liver failure and carcinoma [Friedrich, M. J., Third millennium challenge: hepatitis C. *Jama* 1999, 282 (3), 221-2]. The hepatitis C virus (HCV) is usually transmitted via the blood of an infected person [Bocket, L.; Chevaliez, S.; Talbodec, N.; Sobaszek, A.; Pawlotsky, J. M.; Yazdanpanah, Y., Occupational transmission of hepatitis C virus resulting from use of the same supermarket meat slicer. *Clinical microbiology and infection: the official publication of the European Society of Clinical Microbiology and Infectious Diseases* 2011, 17 (2), 238-41]. Awareness of hepatitis C health problems and forceful efforts to combat the spread on HCV in healthcare settings have led to a significant decline in new infection cases [Organization, W. H., Global hepatitis report 2017. 2017; and Hatzakis, A. et al. The present and future disease burden of hepatitis C virus (HCV) infections with today's treatment paradigm—volume 2. *J Viral Hepat* 2015, 22 Suppl 1, 26-45]. However, the death toll from hepatitis C complications remains as high as 400,000 annually due to the above described unique clinical vs. epidemic profile of hepatitis C. An estimated 70 million people globally are infected with HCV, constituting a major health problem [Collaborators, P. O. H., Global prevalence and genotype distribution of hepatitis C virus infection in 2015: a modelling study. *Lancet Gastroenterol Hepatol* 2017, 2 (3), 161-176]. In 2013, the death rate from hepatitis C complications surpassed that of HIV. In 2015, hepatitis C-related deaths exceeded those of tuberculosis and malaria combined [Stanaway, J. D. et al. The global burden of viral hepatitis from 1990 to 2013: findings from the Global Burden of Disease Study 2013. *Lancet* (London, England) 2016, 388 (10049), 1081-1088].

Up until 2013, interferon (or pegylated interferon) and ribavirin were the most effective available therapies, however the long-term efficacies were as low as 3% [North, C. S.; Hong, B. A.; Adewuyi, S. A.; Pollio, D. E.; Jain, M. K.; Devereaux, R.; Quartey, N. A.; Ashitey, S.; Lee, W. M.; Lisker-Melman, M., Hepatitis C treatment and SVR: the gap between clinical trials and real-world treatment aspirations. *General hospital psychiatry* 2013, 35 (2), 122-8]. Identification of the hepatitis C genome and proteome in early 1990s prompted research efforts that led to development of direct antiviral agents (DAA) in 2011 including bocepreivir and telaprevir. The DAAs revolutionized the treatment of HCV infection[9-11] and the current situation of the treatment looks promising. Nonetheless, new therapies will likely be needed to address emerging resistance of this rapidly mutating virus [Bartenschlager, R.; Baumert, T. F.; Bukh, J.; Houghton, M.; Lemon, S. M.; Lindenbach, B. D.; Lohmann, V.; Moradpour, D.; Pietschmann, T.; Rice, C. M.; Thimme, R.; Wakita, T., Critical challenges and emerging opportunities in hepatitis C virus research in an era of potent antiviral therapy: Considerations for scientists and funding agencies. *Virus research* 2018, 248, 53-62].

The HCV genome is a positive-sense, single-stranded RNA virus belonging to flaviviridae [Murray, C. L.; Jones, C. T.; Rice, C. M., Architects of assembly: roles of Flaviviridae non-structural proteins in virion morphogenesis. *Nature reviews microbiology* 2008, 6 (9), 699-708]. It is composed of about 9,400 nucleotides with highly conserved 5' and 3' terminal regions. The untranslated 5' terminus is followed by a single open reading frame that encodes a polyprotein of 3010 to 3303 amino acids. The virus genome translates mainly to structural and non-structural proteins. The non-structural (NS) proteins including NS3, NS4A, NS4B, NS5A and NS5B comprise proteins that are important for maturation and replication of the virus.

NS3 dually functions as protease (N-terminal domain) and RNA helicase (C-terminal domain). When conformed as protease, NS3 catalyzes the processing of the viral proteome to functional proteins by cleaving NS3-NS4A, NS4A-NS4B, NS4B-NS5A, and NS5A-NS5B junctions. NS5A is a non-enzymatic protein that is important for viral replication however the exact mechanism is poorly understood. NS5B is well characterized to be the viral RNA polymerase. NS4A is a small (54 amino acids) and versatile multi-functioning peptide. It acts as the activating cofactor of NS3 protease (N-terminal) and NS3 helicase (C-terminal) [Ishido, S.; Fujita, T.; Hotta, H., Complex formation of NS5B with NS3 and NS4A proteins of hepatitis C virus. *Biochemical and biophysical research communications* 1998, 244 (1), 35-40;

and Kim, D. W.; Gwack, Y.; Han, J. H.; Choe, J., C-terminal domain of the hepatitis C virus NS3 protein contains an RNA helicase activity. *Biochemical and biophysical research communications* 1995, 215 (1), 160-166]. It is also important for the integration of NS3 to the host cell endoplasmic reticulum [Wölk, B.; Sansonno, D.; Krausslich, H.-G.; Dammacco, F.; Rice, C. M.; Blum, H. E.; Moradpour, D., Subcellular localization, stability, and trans-cleavage competence of the hepatitis C virus NS3-NS4A complex expressed in tetracycline-regulated cell lines. *Journal of virology* 2000, 74 (5), 2293-2304] and neutralization of the immune response of the host cell towards the viral invasion [Li, K.; Foy, E.; Ferreon, J. C.; Nakamura, M.; Ferreon, A. C.; Ikeda, M.; Ray, S. C.; Gale, M.; Lemon, S. M., Immune evasion by hepatitis C virus NS3/4A protease-mediated cleavage of the Toll-like receptor 3 adaptor protein TRIF. *Proceedings of the National Academy of Sciences* 2005, 102 (8), 2992-2997; and Meylan, E.; Curran, J.; Hofmann, K.; Moradpour, D.; Binder, M.; Bartenschlager, R.; Tschopp, J., Cardif is an adaptor protein in the RIG-I antiviral pathway and is targeted by hepatitis C virus. *Nature* 2005, 437 (7062), 1167]. The current approved DAAs elevated the patient sustained cure to 95% in less than two months of use [Kardashian, A. A.; Pockros, P. J., Novel emerging treatments for hepatitis C infection: a fast-moving pipeline. *Therapeutic advances in gastroenterology* 2017, 10 (2), 277-282]. Drugs available for prescription are categorized to three classes: NS3/4A inhibitors, e.g. telaprevir, boceprovir, simeprevir, asunaprevir, paritaprevir, grazopreivir, and voxilaprevir (binding at the substrate site), NS5A inhibitors, e.g. daclatasvir, ledipasvir, ombitasvir, elbasvir, and velpatasvir, and NS5B inhibitors, e.g. soforbuvir, and dasabuvir [Feld, J. J., Direct-Acting Antivirals for Hepatitis C Virus (HCV): The Progress Continues. *Current drug targets* 2017, 18 (7), 851-862].

The use of DAA combinations with high rates of sustained viral recovery (SVR) became routine in therapy regimens [Aghemo, A.; Piroth, L.; Bhagani, S., What do clinicians need to watch for with direct-acting antiviral therapy? *Journal of the International AIDS Society* 2018, 21 Suppl 2, e25076]. For instance, a combination of voxilaprevir (NS3/4A inhibitor), velpatasvir (NS5A inhibitor), and sofosbuvir (NS5B inhibitor) that covers all HCV genotypes 1-6 has been prescribed to patients suffering relapse subsequent to failure of DAA monotherapy [Chahine, E. B.; Kelley, D.; Childs-Kean, L. M., Sofosbuvir/Velpatasvir/Voxilaprevir: A Pan-Genotypic Direct-Acting Antiviral Combination for Hepatitis C. *The Annals of pharmacotherapy* 2018, 52 (4), 352-363].

As outlined in the World Health Organization Global Hepatitis Report, there are several remaining challenges that must be met to eradicate HCV by 2030 [Organization, W. H., Global hepatitis report 2017. 2017]: 1) access to the treatment in economically-challenged areas must be increased [Chhatwal, J.; Chen, Q.; Aggarwal, R., Estimation of Hepatitis C Disease Burden and Budget Impact of Treatment Using Health Economic Modeling. *Infect Dis Clin North Am* 2018, 32 (2), 461-480]; 2) emerging drug resistance must be addressed [Cuypers, L.; Libin, P.; Schrooten, Y.; Theys, K.; Di Maio, V. C.; Cento, V.; Lunar, M. M.; Nevens, F.; Poljak, M.; Ceccherini-Silberstein, F., Exploring resistance pathways for first-generation NS3/4A protease inhibitors boceprevir and telaprevir using Bayesian network learning. *Infection, Genetics and Evolution* 2017, 53, 15-23]; 3) efficacy in broader sectors of HCV patients, such as elder and impaired kidney or liver patients, must be increased [Hellard, M. E.; Chou, R.; Easterbrook, P., WHO guidelines on testing for hepatitis B and C-meeting targets for testing. BioMed Central: 2017]. Thus, there is a clear need to identify new approaches to inhibit viral protein targets and treat HCV infection. The current disclosure introduces a new class of compounds that interfere with NS4A in its binding with NS3 protease and deactivate the enzyme [Joyce, M.; Williams, M.; Hindsgaul, O.; Tyrrell, D. Inhibitors of hepatitis C virus protease, U.S. patent application Ser. No. 10/319,402].

In view of the forgoing, one objective of the present disclosure is to provide therapeutic di-substituted imidazole-based compounds and a process of synthesizing these compounds. A further objective of the present disclosure is to provide a pharmaceutical composition comprising the imidazole-based compound and a method of treating or preventing HCV infection.

BRIEF SUMMARY OF THE INVENTION

According to a first aspect, the present disclosure relates to a compound of formula (I)

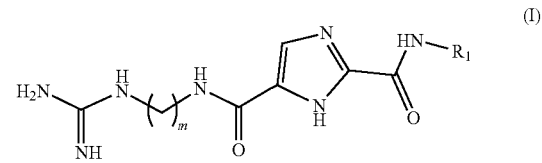

or a salt thereof, a solvate thereof, a tautomer thereof, a stereoisomer thereof, or a mixture thereof, wherein (i) $R_1$ is selected from the group consisting of an optionally substituted alkyl, an optionally substituted cycloalkyl, an optionally substituted arylalkyl, and an optionally substituted aryl, and (ii) m is an integer in a range of 2-8.

In one embodiment, $R_1$ is an optionally substituted $C_{4-10}$ alkyl.

In one embodiment, $R_1$ is a $C_4$-$C_{10}$ alkyl optionally substituted with at least one substituent selected from the group consisting of an alkyloxy, a cycloalkyloxy, an aryloxy, an amine, and an amide.

In one embodiment, $R_1$ is a linear $C_{4-10}$ alkyl.

In one embodiment, $R_1$ is at least one selected from the group consisting of n-pentyl, n-hexyl, n-heptyl, 2-(cyclohexyloxy)ethyl, 3-(cyclohexyloxy)propyl, 2-phenoxyethyl, 3-phenoxypropyl, 4-isopropoxybutyl, 6-methylheptyl, and 3-methylpentyl.

In one embodiment, $R_1$ is n-pentyl.

In one embodiment, $R_1$ is n-hexyl.

In one embodiment, m is 4.

In one embodiment, the compound of formula (I) is

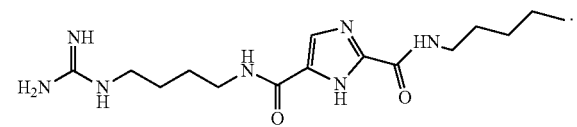 [SMILES: CCCCCNC(=O)c1ncc(CC(=O)NCCCCNC(=N)N)[nH]1]

According to a second aspect, the present disclosure relates to a compound of formula (II)

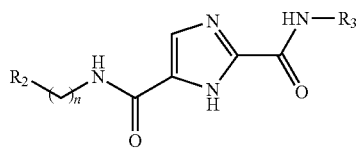

(II)

or a salt thereof, a solvate thereof, a tautomer thereof, a stereoisomer thereof, or a mixture thereof, wherein (i) $R_2$ is selected from the group consisting of an optionally substituted amide, an optionally substituted aryl, and an optionally substituted heteroaryl, $R_3$ is selected from the group consisting of an optionally substituted alkyl, an optionally substituted cycloalkyl, an optionally substituted arylalkyl, an optionally substituted alkenyl, and an optionally substituted aryl, and (iii) n is an integer in a range of 1-4.

In one embodiment, $R_2$ is selected from the group consisting of an unsubstituted amide (—C(O)NH$_2$), N-methylamide (—C(O)NHCH$_3$), a pyridyl, and a furyl.

In one embodiment, $R_3$ is selected from the group consisting of n-pentyl, n-hexyl, n-heptyl, 2-(cyclohexyloxy)ethyl, 3-(cyclohexyloxy)propyl, 2-phenoxyethyl, 3-phenoxypropyl, 4-isopropoxybutyl, 6-methylheptyl, 3-methylpentyl, 2-acetamidoethyl, and 3,7-dimethylocta-2,6-dien-1-yl.

According to a third aspect, the present disclosure relates to a pharmaceutical composition involving the compound of formula (I) of the first aspect and a pharmaceutically acceptable carrier and/or excipient.

In one embodiment, the pharmaceutical composition contains 0.5-500 M of the compound of formula (I) relative to a total volume of the composition.

In one embodiment, the pharmaceutically acceptable carrier and/or excipient is at least one selected from the group consisting of a buffer, an inorganic salt, a fatty acid, a vegetable oil, a synthetic fatty ester, a surfactant, and a polymer.

In one embodiment, the pharmaceutical composition further includes an antiviral agent.

In one embodiment, the compound of formula (I) is

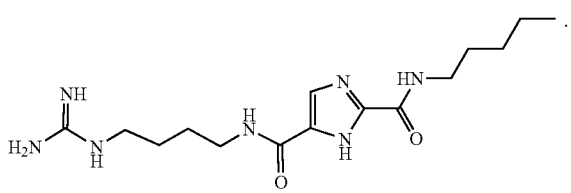

According to a fourth aspect, the present disclosure relates to a method of preventing or treating hepatitis C virus (HCV) infection. The method involves administering the pharmaceutical composition of the third aspect to a subject in need of therapy.

In one embodiment, 0.1-100 mg/kg of the compound of formula (I) is administered per body weight of the subject.

In one embodiment, the compound of formula (I) binds to an activation site of hepatitis C virus (HCV) serine protease.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
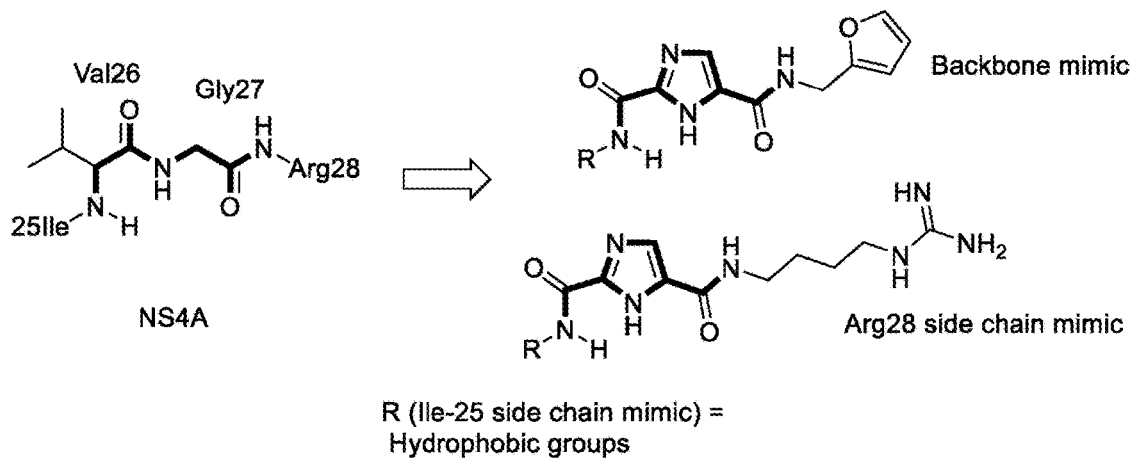
FIG. 1 is a schematic diagram illustrating the design of imidazole scaffolds based on the planar region of NS4A.

Embodiments of the present disclosure will now be described more fully hereinafter with reference to the accompanying drawings, in which some, but not all embodiments of the disclosure are shown.

As used herein, the words "a" and "an" and the like carry the meaning of "one or more". Within the description of this disclosure, where a numerical limit or range is stated, the endpoints are included unless stated otherwise. Also, all values and subranges within a numerical limit or range are specifically included as if explicitly written out.

As used herein, the terms "complex", "compound", and "product" are used interchangeably, and are intended to refer to a chemical entity, whether in the solid, liquid or gaseous phase, and whether in a crude mixture or purified and isolated.

As used herein, the term "solvate" refers to a physical association of a compound of this disclosure with one or more solvent molecules, whether organic or inorganic. This physical association includes hydrogen bonding. In certain instances, the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. Solvate encompasses both solution phase and isolable solvates. Exemplary solvents include, but are not limited to, water, methanol, ethanol, n-propanol, isopropanol, n-butanol, isobutanol, tert-butanol, ethyl acetate and other lower alkanols, glycerine, acetone, dichloromethane (DCM), dimethyl sulfoxide (DMSO), dimethyl acetate (DMA), dimethylformamide (DMF), isopropyl ether, acetonitrile, toluene, N-methylpyrrolidone (NMP), tetrahydrofuran (THF), tetrahydropyran, other cyclic mono-, di- and tri-ethers, polyalkylene glycols (e.g. polyethylene glycol, polypropylene glycol, propylene glycol), and mixtures thereof in suitable proportions. Exemplary solvates include, but are not limited to, hydrates, ethanolates, methanolates, isopropanolates and mixtures thereof. Methods of solvation are generally known to those of ordinary skill in the art.

As used herein, the term "tautomer" refers to constitutional isomers of organic compounds that readily convert by tautomerization or tautomerism. The interconversion commonly results in the formal migration of a hydrogen atom or proton, accompanied by a switch of a single bond and adjacent double bond. Tautomerism is a special case of structural isomerism, and because of the rapid interconversion, tautomers are generally considered to be the same chemical compound. In solutions in which tautomerization is possible, a chemical equilibrium of the tautomers will be reached. The exact ratio of the tautomers depends on several factors including, but not limited to, temperature, solvent and pH. Exemplary common tautomeric pairs include, but are not limited to, ketone and enol, enamine and imine, ketene and ynol, nitroso and oxime, amide and imidic acid, lactam and lactim (an amide and imidic tautomerism in heterocyclic rings), and open-chain and cyclic forms of an acetal or hemiacetal (e.g., in reducing sugars).

As used herein, the term "stereoisomer" refers to isomeric molecules that have the same molecular formula and sequence of bonded atoms (i.e. constitution), but differ in the three-dimensional orientations of their atoms in space. This contrasts with structural isomers, which share the same molecular formula, but the bond connection of their order differs. By definition, molecules that are stereoisomers of each other represent the same structural isomer. Enantiomers are two stereoisomers that are related to each other by reflection, they are non-superimposable mirror images. Every stereogenic center in one has the opposite configuration in the other. Two compounds that are enantiomers of each other have the same physical properties, except for the direction in which they rotate polarized light and how they interact with different optical isomers of other compounds. Diastereomers are stereoisomers not related through a reflection operation, they are not mirror images of each other. These include meso compounds, cis- and trans- (E- and Z-) isomers, and non-enantiomeric optical isomers. Diastereomers seldom have the same physical properties. In terms of the present disclosure, stereoisomers may refer to enantiomers, diastereomers, or both.

Conformers, rotamers, or conformational isomerism refers to a form of isomerism that describes the phenomenon of molecules with the same structural formula but with different shapes due to rotations around one or more bonds. Different conformations can have different energies, can usually interconvert, and are very rarely isolatable. There are some molecules that can be isolated in several conformations. Atropisomers are stereoisomers resulting from hindered rotation about single bonds where the steric strain barrier to rotation is high enough to allow for the isolation of the conformers. In terms of the present disclosure, stereoisomers may refer to conformers, atropisomers, or both.

In terms of the present disclosure, stereoisomers of the double bonds, ring systems, stereogenic centers, and the like can all be present in the compounds, and all such stable isomers are contemplated in the present disclosure. Cis- and trans- (or E- and Z-) stereoisomers of the compounds of the present disclosure wherein rotation around the double bond is restricted, keeping the substituents fixed relative to each other, are described and may be isolated as a mixture of isomers or as separated isomeric forms. S- and R- (or L- and D-) stereoisomers of the compounds of the present disclosure are described and may be isolated as a mixture of isomers or as separated isomeric forms. All processes or methods used to prepare compounds of the present disclosure and intermediates made therein are considered to be part of the present disclosure. When stereoisomeric products are prepared, they may be separated by conventional methods, for example, by chromatography, fractional crystallization, or use of a chiral agent.

As used herein, the term "substituted" refers to at least one hydrogen atom that is replaced with a non-hydrogen group, provided that normal valencies are maintained and that the substitution results in a stable compound. When a substituent is noted as "optionally substituted", the substituents are selected from halo, hydroxyl, alkoxy, oxo, alkanoyl, aryloxy, alkanoyloxy, amino, alkylamino, arylamino, arylalkylamino, disubstituted amines (e.g. in which the two amino substituents are selected from the exemplary group including, but not limited to, alkyl, aryl or arylalkyl), alkanoylamino, aroylamino, aralkanoylamino, substituted alkanoylamino, substituted arylamino, substituted aralkanoylamino, thiol, alkylthio, arylthio, arylalkylthio, alkylthiono, arylthiono, aryalkylthiono, alkylsulfonyl, arylsulfonyl, arylalkylsulfonyl, sulfonamide (e.g. $-SO_2NH_2$), substituted sulfonamide, nitro, cyano, carboxy, unsubstituted amide (i.e. $-CONH_2$), substituted amide (e.g. $-CONHalkyl$, $-CONHaryl$, $-CONHarylalkyl$ or cases where there are two substituents on one nitrogen from alkyl, aryl, or alkylalkyl), alkoxycarbonyl, aryl, substituted aryl, guanidine, heterocyclyl (e.g. indolyl, imidazoyl, furyl, thienyl, thiazolyl, pyrrolidyl, pyridyl, pyrimidiyl, pyrrolidinyl, piperidinyl, morpholinyl, piperazinyl, homopiperazinyl and the like), substituted heterocyclyl and mixtures thereof. The substituents may themselves be optionally substituted, and may be either unprotected, or protected as necessary, as known to those skilled in the art, for example, as taught in Greene, et al., "Protective Groups in Organic Synthesis", John Wiley and Sons, Second Edition, 1991, hereby incorporated by reference in its entirety.

As used herein, the term "alkyl" unless otherwise specified refers to both branched and straight chain saturated aliphatic primary, secondary, and/or tertiary hydrocarbons of typically $C_1$ to $C_{21}$, for example $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, and specifically includes, but is not limited to, methyl, trifluoromethyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, 2,3-dimethylbutyl, 2-ethylhexyl, heptyl, octyl, nonyl, 3,7-dimethyloctyl, decyl, undecyl, dodecyl, tridecyl, 2-propylheptyl, tetradecyl, pentadecyl, hexadecyl, heptadecyl, octadecyl, nonadecyl, and eicosyl.

The term "cycloalkyl" refers to cyclized alkyl groups. Exemplary cycloalkyl groups include, but are not limited to, cyclopropyl, cyclobutyl, cyclopentyl, cyclohexyl, norbornyl, and adamantyl. Branched cycloalkyl groups such as exemplary 1-methylcyclopropyl and 2-methylcyclopropyl groups are included in the definition of cycloalkyl as used in the present disclosure.

The term "alkenyl" refers to a straight, branched, or cyclic hydrocarbon fragment containing at least one C=C double bond. Exemplary alkenyl groups include, without limitation, 1-propenyl, 2-propenyl (or "allyl"), 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, and 9-decenyl.

The term "arylalkyl", as used herein, refers to a straight or branched chain alkyl moiety having 1 to 8 carbon atoms that is substituted by an aryl group as defined herein, and includes, but is not limited to, benzyl, phenethyl, 2-methylbenzyl, 3-methylbenzyl, 4-methylbenzyl, 2,4-dimethylbenzyl, 2-(4-ethylphenyl)ethyl, 3-(3-propylphenyl)propyl, and the like.

The term "aryl", as used herein, and unless otherwise specified, refers to phenyl, biphenyl, naphthyl, anthracenyl, and the like.

The term "heteroaryl" refers to an aryl group where at least one carbon atom is replaced with a heteroatom (e.g. nitrogen, oxygen, sulfur) and can be indolyl, furyl, imidazolyl, triazolyl, triazinyl, oxazolyl, isoxazolyl, thiazolyl, isothiazolyl, pyrazolyl, pyrrolyl, pyrazinyl, tetrazolyl, pyridyl (or its N-oxide), thienyl, pyrimidinyl (or its N-oxide), 1H-indolyl, isoquinolyl (or its N-oxide), or quinolyl (or its N-oxide), for example.

The terms "alkoxy" and "alkyloxy" refer to a straight or branched alkyl group attached to an oxygen atom. Exemplary alkyloxy groups include, but are not limited to, methoxy, ethoxy, propoxy, isopropoxy, butoxy, isobutoxy, secondary butoxy, tertiary butoxy, pentoxy, isopentoxy, hexyloxy, heptyloxy, octyloxy, nonyloxy, and decyloxy.

The terms "cycloalkoxy" and 'cycloalkyloxy" as used herein means a cycloalkyl group linked to an oxygen atom, such as, for example, cyclobutyloxy or cyclopropyloxy.

The term "aryloxy" refers to an aryl group bonded to an oxygen atom. Exemplary aryloxy groups include, but are not limited to, phenoxy, 4-methylphenoxy, and naphthaloxy.

The term "amide", as used herein, and unless otherwise specified, refers to an amide (—C(O)NR$_c$R$_d$) that is unsubstituted (—C(O)NH$_2$), monosubstituted (where R is a hydrogen), or disubstituted where R$_c$ and R$_d$ are independently an optionally substituted alkyl, an optionally substituted cycloalkyl, an optionally substituted arylalkyl, or an optionally substituted aryl.

As used herein, the term "amine" includes unsubstituted amine (—NH$_2$), monosubstituted amine (—NHR$_a$), as well as disubstituted amine (—NR$_a$R$_b$), wherein R$_a$ and R$_b$ are independently an optionally substituted alkyl, an optionally substituted cycloalkyl, an optionally substituted arylalkyl, or an optionally substituted aryl.

The present disclosure is intended to include all isotopes of atoms occurring in the present compounds. Isotopes include those atoms having the same atomic number but different mass numbers. By way of general example, and without limitation, isotopes of hydrogen include deuterium and tritium, isotopes of carbon include $^{13}$C and $^{14}$C, isotopes of nitrogen include $^{14}$N and $^{15}$N, and isotopes of oxygen include $^{16}$O, $^{17}$O and $^{18}$O. Isotopically labeled compounds of the disclosure can generally be prepared by conventional techniques known to those skilled in the art or by processes and methods analogous to those described herein, using an appropriate isotopically labeled reagent in place of the non-labeled reagent otherwise employed.

According to a first aspect, the present disclosure relates to a compound of formula (I)

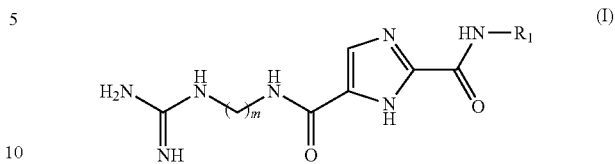

or a salt thereof, a solvate thereof, a tautomer thereof, a stereoisomer thereof, or a mixture thereof.

R$_1$ is selected from the group consisting of an optionally substituted alkyl, an optionally substituted cycloalkyl, an optionally substituted arylalkyl, and an optionally substituted aryl.

In one or more embodiments, R$_1$ is an optionally substituted alkyl, which may be linear or branched.

In one or more embodiments, R$_1$ is a substituted alkyl, preferably a substituted C$_{3-10}$ alkyl, preferably a substituted C$_{4-9}$ alkyl, preferably a substituted C$_{5-8}$ alkyl, preferably a substituted C$_{6-7}$ alkyl. The carbon counts described herein refers to a number of carbon atoms of the alkyl group of R$_1$ which excludes the carbon atoms of optionally present substituents. The alkyl of R$_1$ may be substituted with at least one substituent selected from the group consisting of an alkyloxy, a cycloalkyloxy, and an aryloxy, for example, methoxy, ethoxy, isopropoxy, cyclopentyloxy, cyclohexyloxy, and phenoxy. Alternatively, the alkyl of R$_1$ may be substituted with an amine and/or an amide. The alkyl of R$_1$ may be preferably substituted with an amide group such as acetamide, propanamide, and isobutyramide. In a preferred embodiment, the alkyl of R$_1$ is substituted with acetamide.

In an alternative embodiment, R$_1$ is an unsubstituted alkyl, preferably a linear alkyl, preferably a linear C$_{3-10}$ alkyl, preferably a linear C$_{4-9}$ alkyl, preferably a linear C$_{5-8}$ alkyl, preferably a linear C$_{6-7}$ alkyl. Exemplary linear alkyls include, but are not limited to n-propyl, n-butyl, n-pentyl, n-hexyl, n-heptyl, n-octyl, n-nonyl, n-decyl. Alternatively, R$_1$ is a branched alkyl, such as 6-methylheptyl, 3-methylpentyl, 2,2-dimethylbutyl, 2,3-dimethylbutyl, 2-ethylhexyl, 3,7-dimethyloctyl, and 2-propylheptyl. In a preferred embodiment, R$_1$ is 6-methylheptyl, or 3-methylpentyl.

In one or more embodiments, R$_1$ is at least one selected from the group consisting of n-pentyl, n-hexyl, n-heptyl, 2-(cyclohexyloxy)ethyl, 3-(cyclohexyloxy)propyl, 2-phenoxyethyl, 3-phenoxypropyl, 4-isopropoxybutyl, 6-methylheptyl, 3-methylpentyl and 2-acetamidoethyl. In a preferred embodiment, R$_1$ is n-pentyl. In another preferred embodiment, R$_1$ is n-hexyl. In a most preferred embodiment, R$_1$ is n-pentyl.

As used herein, the value of m denotes an alkyl chain of —CH$_2$— groups connected between guanidino and amide groups of the compound of formula (I). In one or more embodiments, m is an integer in a range of 2-9, preferably 3-8, preferably 4-7, preferably 5-6. Most preferably, m is 4.

In some embodiments, the compound of formula (I) is one or more of the following structures:

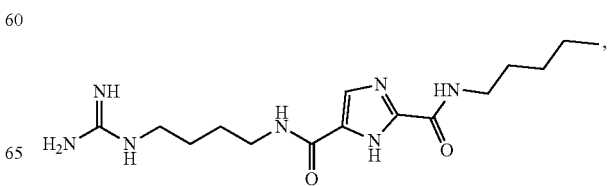

-continued

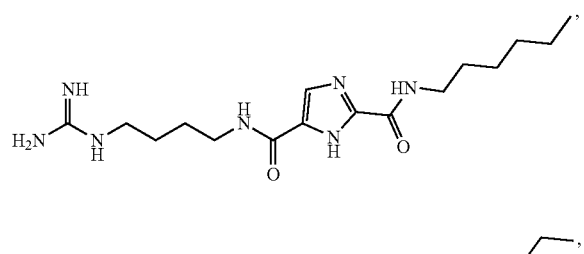

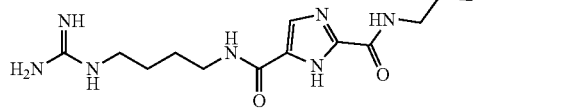

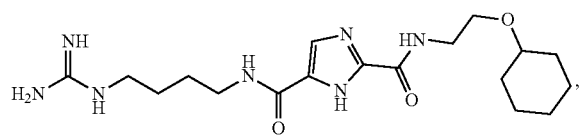

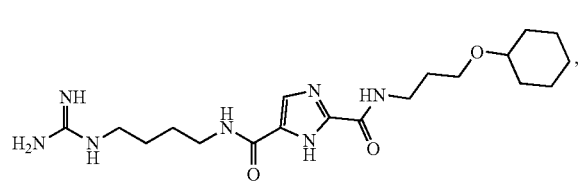

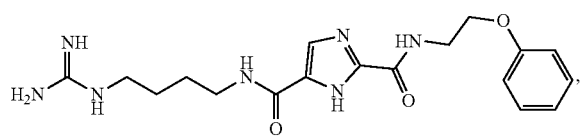

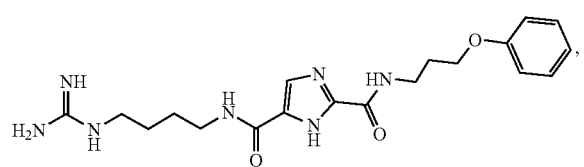

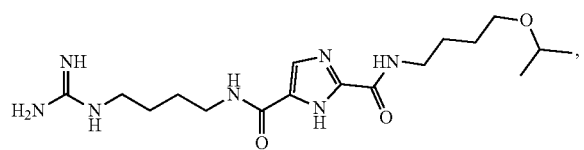

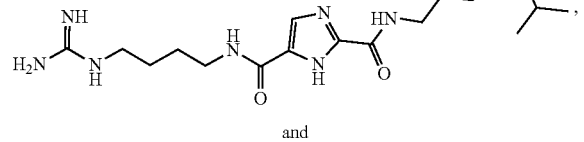

and

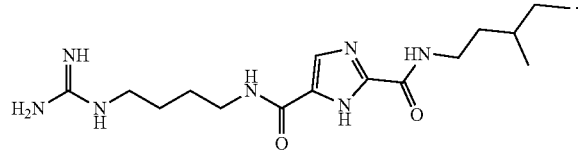

In a most preferred embodiment, the compound of formula (I) is

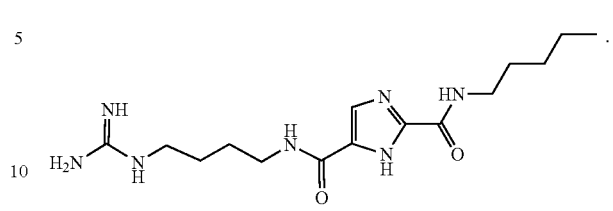

According to a second aspect, the present disclosure relates to a compound of formula (II)

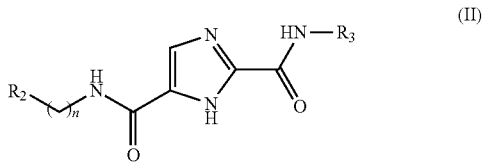

or a salt thereof, a solvate thereof, a tautomer thereof, a stereoisomer thereof, or a mixture thereof.

$R_2$ is selected from the group consisting of an optionally substituted amide, an optionally substituted aryl, and an optionally substituted heteroaryl.

In one or more embodiments, $R_2$ is a monosubstituted alkylamide, preferably a monosubstituted $C_{2-5}$ alkylamide, preferably a monosubstituted $C_{3-4}$ alkylamide, such as N-methylamide (—C(O)NHCH$_3$), N-ethylamide (—C(O)NHC$_2$H$_5$), and N-(n-propyl)amide (—C(O)NHC$_3$H$_7$). Most preferably, $R_2$ is N-methylamide. In another embodiment, $R_2$ is an unsubstituted amide (—C(O)NH$_2$).

Alternatively, $R_2$ is an optionally substituted heteroaryl. In a preferred embodiment, $R_2$ is an optionally substituted pyridyl, or an optionally substituted furyl. Most preferably, $R_2$ is a pyridyl, or a furyl.

As used herein, the value of n denotes an alkyl chain of —CH$_2$— groups connected between —R$_2$ and amide groups of the compound of formula (II). In one or more embodiments, n is an integer in a range of 1-4, or 2-3. In a preferred embodiment, n is 1.

$R_3$ is selected from the group consisting of an optionally substituted alkyl, an optionally substituted cycloalkyl, an optionally substituted arylalkyl, an optionally substituted alkenyl, and an optionally substituted aryl.

In one embodiment, $R_2$ is a monosubstituted alkylamide, and $R_3$ is a substituted alkyl, preferably a substituted $C_{3-10}$ alkyl, preferably a substituted $C_{4-9}$ alkyl, preferably a substituted $C_{5-8}$ alkyl, preferably a substituted $C_{6-7}$ alkyl. The alkyl of $R_3$ may be substituted with at least one substituent selected from the group consisting of an alkyl, an alkyloxy, a cycloalkyloxy, and an aryloxy, for example, methoxy, ethoxy, isopropoxy, cyclopentyloxy, cyclohexyloxy, and phenoxy. Alternatively, $R_2$ is a monosubstituted alkylamide, and $R_3$ is a linear (i.e. unsubstituted) alkyl, preferably a linear $C_{3-10}$ alkyl, preferably a linear $C_{4-9}$ alkyl, preferably a linear $C_{5-8}$ alkyl, preferably a linear $C_{6-7}$ alkyl. Exemplary linear alkyls include, but are not limited to n-propyl, n-butyl, n-pentyl, n-hexyl, n-heptyl, n-octyl, n-nonyl, n-decyl. In a preferred embodiment, the linear alkyl is n-pentyl, n-hexyl, or n-heptyl. In another embodiment, $R_2$ is an unsubstituted amide (—C(O)NH$_2$), and $R_3$ is a substituted alkyl, preferably a substituted $C_{3-10}$ alkyl, preferably a substituted $C_{4-9}$ alkyl, preferably a substituted $C_{5-8}$ alkyl, preferably a substituted $C_{6-7}$ alkyl, most preferably 6-methylheptyl, or 3-methylpentyl. Alternatively, $R_2$ is a monosubstituted alkylamide, and $R_3$ is an optionally substituted alkenyl, preferably $R_3$ is a substituted $C_{5-16}$ alkenyl, preferably a substituted $C_{6-14}$ alkenyl, preferably a substituted $C_{7-12}$ alkenyl, preferably a substituted $C_{8-10}$ alkenyl. Most preferably, $R_3$ is 3,7-dimethylocta-2,6-dien-1-yl.

In another embodiment, $R_2$ is a heteraryl, and $R_3$ is a substituted alkyl, preferably a substituted $C_{3-10}$ alkyl, preferably a substituted $C_{4-9}$ alkyl, preferably a substituted $C_{5-8}$ alkyl, preferably a substituted $C_{6-7}$ alkyl. The alkyl of $R_3$ may be substituted with an amide group. Exemplary amide groups include, but are not limited to, acetamide, propanamide, and isobutyramide. In a preferred embodiment, the alkyl of $R_3$ is substituted with acetamide. Alternatively, $R_2$ is a heteraryl, and $R_3$ is a linear (i.e. unsubstituted) alkyl, preferably a linear $C_{3-10}$ alkyl, preferably a linear $C_{4-9}$ alkyl, preferably a linear $C_{5-8}$ alkyl, preferably a linear $C_{6-7}$ alkyl. Exemplary linear alkyls include, but are not limited to, n-propyl, n-butyl, n-pentyl, n-hexyl, n-heptyl, n-octyl, n-nonyl, n-decyl. In a preferred embodiment, the linear alkyl is n-hexyl.

In at least one embodiment, $R_3$ is selected from the group consisting of n-pentyl, n-hexyl, n-heptyl, 2-(cyclohexyloxy) ethyl, 3-(cyclohexyloxy)propyl, 2-phenoxyethyl, 3-phenoxypropyl, 4-isopropoxybutyl, 6-methylheptyl, 3-methylpentyl, 2-acetamidoethyl, and 3,7-dimethylocta-2,6-dien-1-yl.

In some embodiments, the compound of formula (II) has one of the following structures:

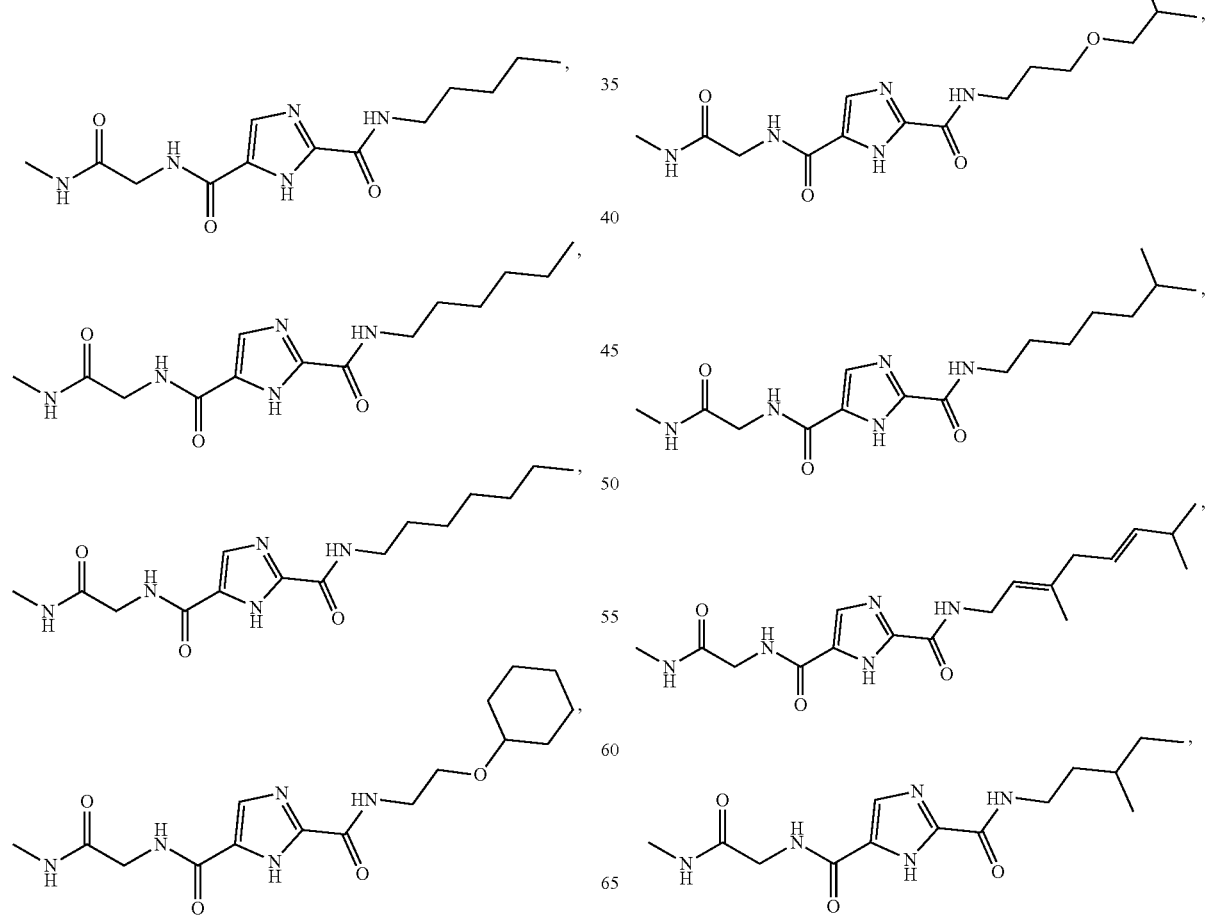

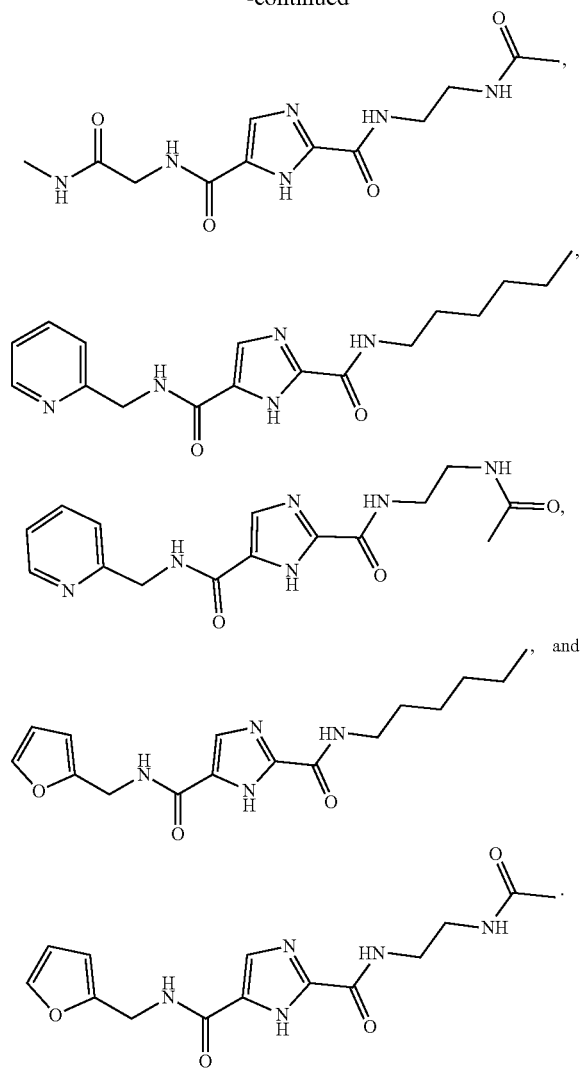

, and

The compounds of the present disclosure may be prepared by methods known to those of ordinary skills in the art. The following methods set forth below are provided for illustrative purposes and are not intended to limit the scope of the disclosure. It will be recognized that it may be preferred or necessary to prepare such a compound in which a functional group is protected using a conventional protecting group then to remove the protecting group to provide a compound of the present disclosure.

Figure 2:
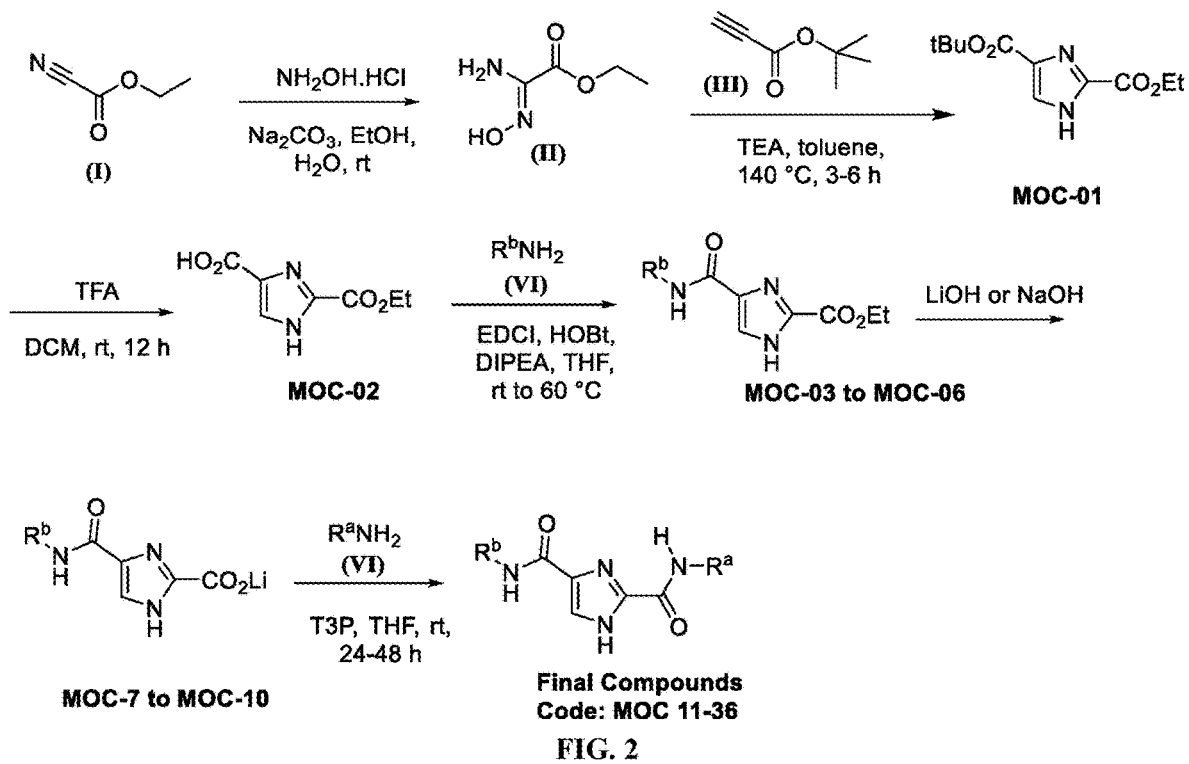
FIG. 2 is a synthesis scheme for the preparation of starting materials and compounds of formulae (I) and (II).
Figure 3:
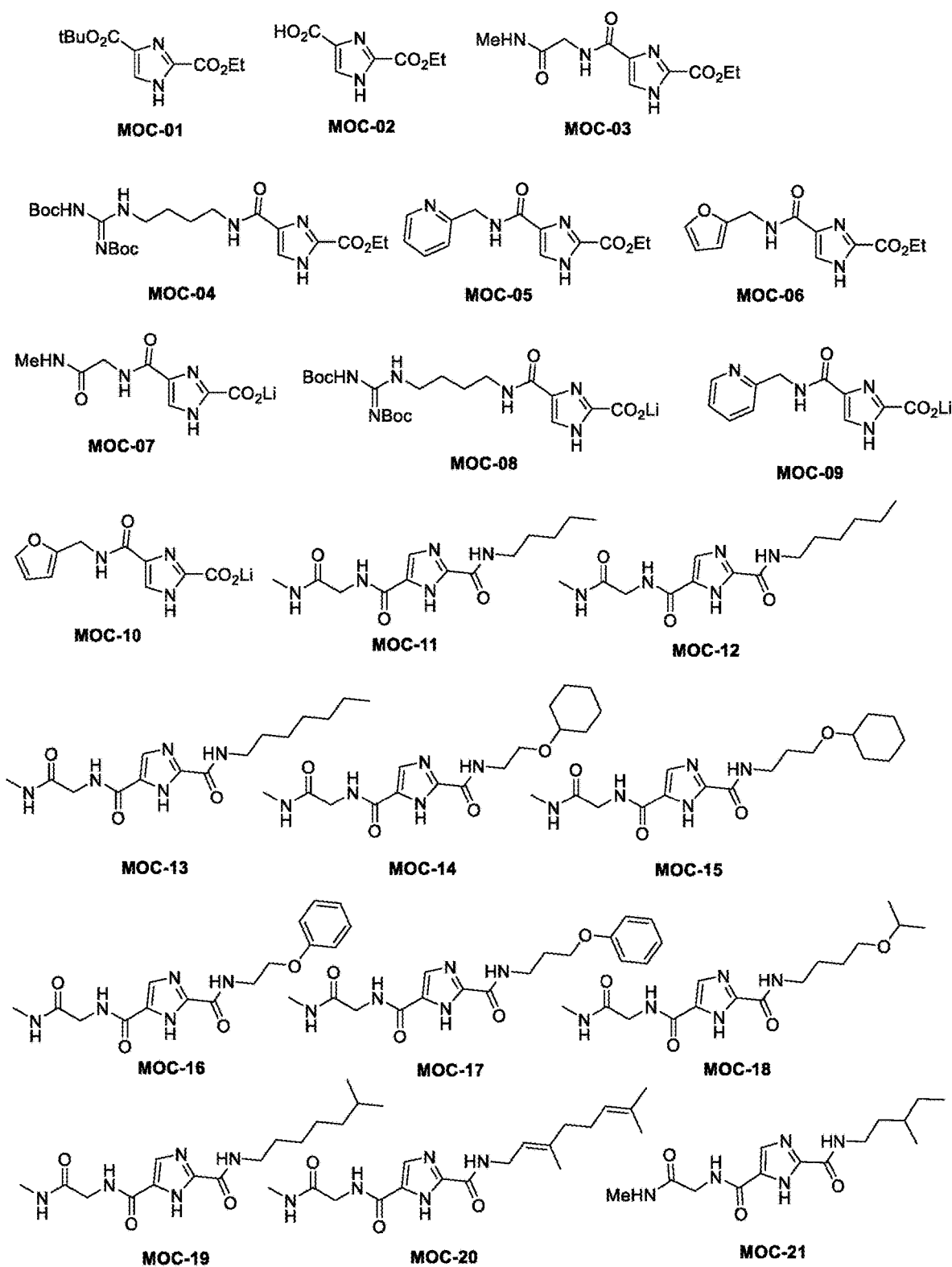
FIG. 3 shows a list of MOC compounds of the present disclosure.
Figure 3:
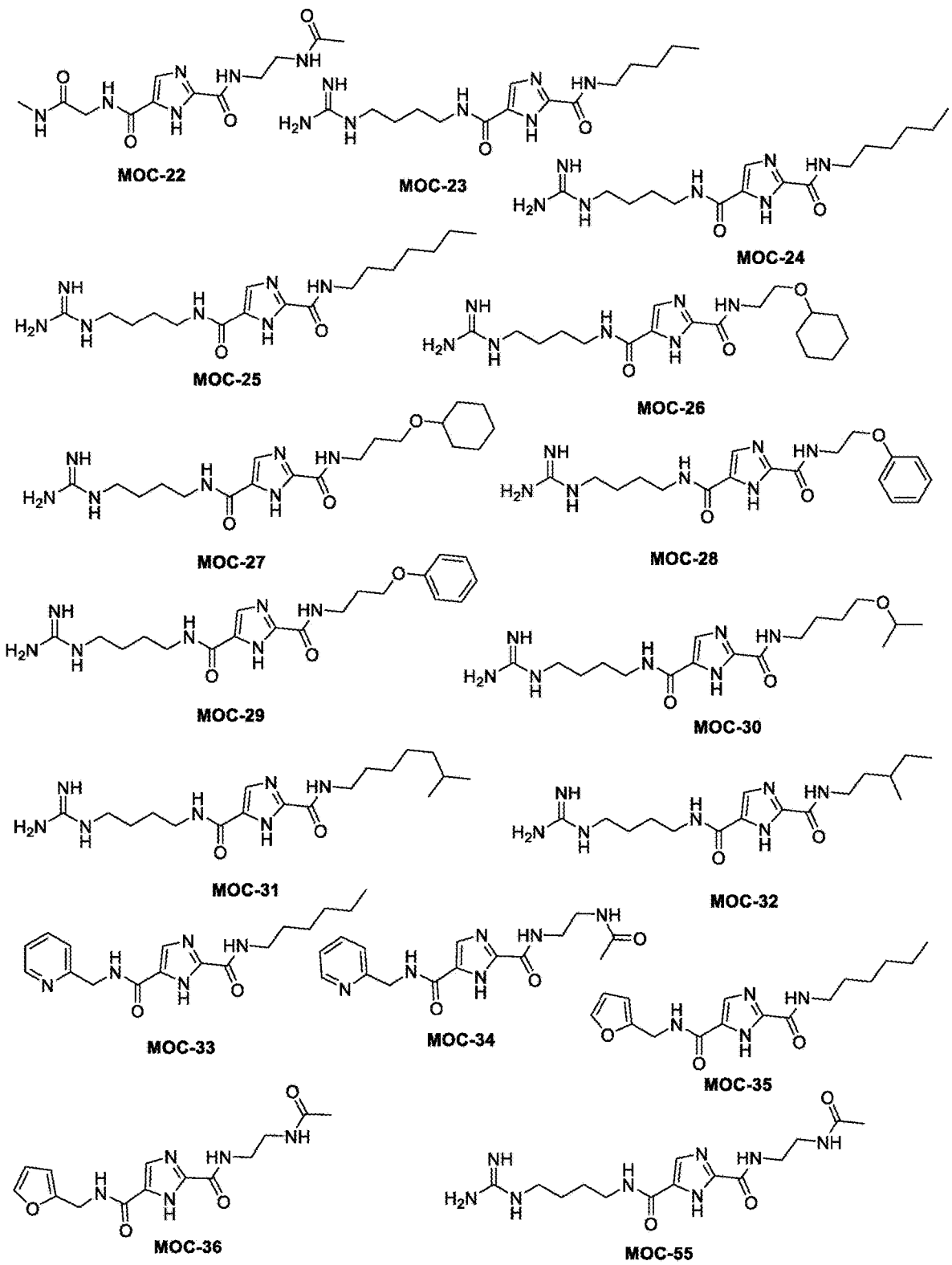

The compounds of formulae (I) and (II) may, for example, be synthesized according to a process illustrated in FIG. 2. Briefly, a 2,4-di substituted imidazole (i.e. 2-(ethoxycarbonyl)-1H-imidazole-4-carboxylic acid (MOC-02)) may be formed via (i) a cyclization reaction between an oxime (i.e. (Z)-2-amino-2-(hydroxyimino) acetate) and an alkyne (i.e. tert-butyl propiolate) thereby forming a disubstituted imidazole tert-butyl ester (i.e. 5-(tert-butyl) 2-ethyl 1H-imidazole-2,5-dicarboxylate (MOC-01)), and (ii) deprotection of tert-butyl ester group of MOC-01 thereby forming MOC-02 [Duguay, G.; Guémas, J.-P.; Meslin, J.-C.; Pradere, J.-P.; Reliquet, F.; Reliquet, A.; Tea-Gokou, C.; Quiniou, H.; Rabiller, C., Heteroatomic chains and their products of cyclisation. IV. t-butyl-2-phthalimido-2-(3,6-dihydro-1,3-2H-thiazine-2-yliden)-acetates substituted in position 5 by a functional group. *Journal of Heterocyclic Chemistry* 1980, 17 (4), 767-770; and Vuilhorgne, M.; Malpart, J.; Mutti, S.; Mignani, S., Preparative route to 2-ethoxycarbonylimidazole-4-phosphonate and diethylimidazole-2,4-dicarboxylate. *Journal of Heterocyclic Chemistry* 2003, 40 (1), 159-162, each incorporated herein by reference in their entirety]. Alternatively, MOC-02 may be available from commercial vendors including, without limitation, Accel Pharmtech, Asta Tech, Ambeed, Alichem, BLD Pharmatech, and FCH group.

In one embodiment, the guanidino side chain of compound of formula (I) may be incorporated via amidation reaction between the carboxylic group of MOC-02 and an amine of formula (III)

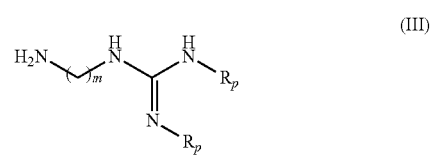

(III)

wherein m is as previously specified, and $R_p$ is a protecting group intended to avoid formation of undesired bonds during the amidation. The details concerning the use of protecting groups in accordance with the present invention are known to those of ordinary skills in the art. Protecting groups that can be used are listed, for example, in Greene, et al., "Protective Groups in Organic Synthesis", Wiley-Interscience, 1999, hereby incorporated by reference in its entirety. Exemplary protecting groups include, but are not limited to, acyl groups such as formyl, trifluoroacetyl, phthalyl, and p-toluenesulfonyl, aromatic carbamate groups such as benzyloxycarbonyl (Cbz or Z), and substituted bensyloxycarbonyls, and 9-fluorenylmethyloxycarbonyl (Fmoc), aliphatic carbamate groups such as tert-butyloxycarbonyl (Boc), ethoxycarbonyl, diisopropylmethoxycarbonyl, and allyloxycarbonyl, cyclic alkyl carbamate groups such as cyclopentyloxycarbonyl and adamantyloxycarbonyl, alkyl groups such as triphenylmethyl and benzyl, trialkylsilyl such as trimethylsilyl, and thiol containing groups such as phenylthiocarbonyl, and dithiasuccinoyl. In a preferred embodiment, $R_p$ of the amine of formula (III) is Boc. After the first amidation reaction, a guanidino compound of formula (IV) may be obtained

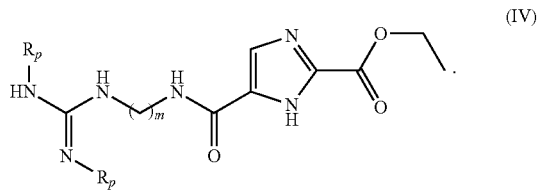

(IV)

The protecting group R, may be cleaved after the amidation reaction using deprotection protocols generally known to those of ordinary skill in the art. For example, when the Boc group is used, the methods of choice may be trifluoroacetic acid, neat or in dichloromethane, or HCl in dioxane or in ethyl acetate.

In another embodiment, the $R_2$ amide side chain of the compound of formula (II) may be incorporated via a first amidation reaction between the carboxylic group of MOC-02 and an amine of formula (V):

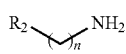

(V)

wherein $R_2$ and n are as previously specified. After the first amidation reaction, a compound of formula (VI) may be obtained

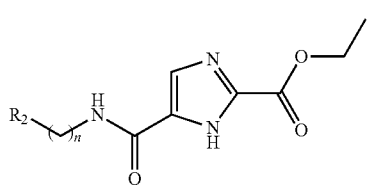

(VI)

Generally, the first amidation reaction may be performed in a solvent such as tetrahydrofuran, benzene, xylene, dimethylformamide, ethyl acetate, diethyl ether, acetonitrile, dimethyl sulfoxide, methylene chloride, chloroform, nitrobenzene, isopropanol, and mixtures thereof. Preferably, tetrahydrofuran is used as the solvent. In a preferred embodiment, a molar ratio of the amine of formula (III) or (V) to the disubstituted imidazole (i.e. MOC-02) is in a range of 1:1 to 3:1, preferably 1.05:1 to 2:1, preferably 1.1:1 to 1.5:1, or about 1.2:1.

In preferred embodiments, a base such as trimethylamine, trimethylamine, diisopropylethylamine (DIPEA), triisopropylamine, dimethylaminopropylamine, N-methylmorpholine, N-methylpyrrolidine, 4-dimethylaminopyridine (DMAP), and 1,8-diazabicyclo[5.4.0]undec-7-ene (DBU) is present in the first amidation reaction. Preferably, the base is DIPEA. In a preferred embodiment, a molar ratio of the base to the disubstituted imidazole (i.e. MOC-02) is in a range of 1:1 to 5:1, preferably 1.2:1 to 3:1, preferably 1.5:1 to 2:1, or about 1.75:1.

In a related embodiment, amide bond formation coupling reagents may be used to facilitate and/or accelerate the first amidation reaction. Examples of such coupling reagents include, without limitation, carbodiimides such as 1-ethyl-3-(3-dimethylaminopropyl)carbodiimide (EDC or EDCI), N,N-dicyclohexylcarbodiimide (DCC), N,N'-diisopropylcarbodiimide (DIC), 1H-benzotriazole derivatives such as 1-[bis(dimethylamino)methylene]-1H-1,2,3-triazolo[4,5-b]pyridinium 3-oxid hexafluorophosphate (HATU), O-(benzotriazol-1-yl)-1,1,3,3-tetramethyluronium hexafluorophosphate (HBTU), O-benzotriazol-1-yl-1,1,3,3-tetramethyluronium tetrafluoroborate (TBTU), and N-[(5-chloro-3-oxido-1H-benzotriazol-1-yl)-4-morpholinylmethylene]-N-methylmethanaminium hexafluorophosphate (HDMC), and carbonyldiimidazole (CDI).

In another related embodiment, an additive that minimizes racemization during the amidation reaction may be used in combination of the aforementioned coupling reagent. Exemplary additives include, but are not limited to, 1-hydroxy-7-azabenzotriazole (HOAt), hydroxybenzotriazole (HOBt), 6-chloro-1-hydroxybenzotriazole (6-ClHOBt), ethyl 1-hydroxy-1H-1,2,3-triazole-4-carboxylate (HOCt), 1-hydroxy-2-pyridinone (HOPy), ethyl 2-cyano-2-(hydroxyimino)acetate (Oxyma), N-hydroxy-5-norbornene2,3-dicarboximide (HONB), N-hydroxysuccinimide (HOSu), 3-hydroxy-4-oxo-3,4-dihydro1,2,3-benzotriazine (HODhbt), and copper(I) iodide. Preferably, the additive is HOBt.

In a most preferred embodiment, the coupling reagent is EDCI and the additive is HOBt. A molar ratio of the coupling reagent (e.g. EDCI) to the disubstituted imidazole (i.e. MOC-02) is in a range of 1:1 to 3:1, preferably 1.2:1 to 2:1, or about 1.5:1. A molar ratio of the coupling reagent (e.g. EDCI) to the additive (e.g. HOBt) is in a range of 1:2 to 2:1, preferably 1:1.5 to 1.5:1, or about 1:1.

In a preferred embodiment, the base, the coupling reagent, and the additive are each introduced to the first amidation reaction mixture in a two-stage or multi-stage fashion. For example, a first portion of the base, the coupling reagent, or the additive which is 50-75%, 55-70%, or 57-67% of a total mole of the base, the coupling reagent, or the additive used herein may be added to the reaction mixture and allowed to react for 1-5 hours, 2-4 hours, or about 3 hours, and subsequently a second portion of the base, the coupling reagent, or the additive which is 25-50%, 30-45%, or 33-43% of a total mole of the base, the coupling reagent, or the additive used herein may be added to the same reaction mixture. Alternatively, the base, the coupling reagent, and the additive may be introduced to the reaction mixture in one batch. In one or more embodiments, the first amidation reaction mixture is reacted at a temperature of 20-80° C., preferably 30-70° C., preferably 40-60° C. under agitation. The first amidation reaction may be conducted in inert gas (e.g. nitrogen, argon, helium). Also, in some embodiments, the reaction may not be conducted in inert gas, but in a vacuum.

Methods of agitation include, without limitation, using an agitator, a vortexer, a rotary shaker, a magnetic stirrer, a centrifugal mixer, or an overhead stirrer. In another embodiment, the mixture and/or the reaction mixture is left to stand (i.e. not stirred). Alternatively, the mixture and/or the reaction mixture is sonicated in an ultrasonic bath or with an ultrasonic probe.

The compound of formula (I) may be produced via a second amidation reaction. In one embodiment, the amidation reaction involves (i) adding a base to the compound of formula (IV) to form a carboxylate salt, and (ii) reacting the carboxylate salt with a proper amine of formula (VII)

$$H_2N-R_1,$$ (VII)

thereby forming the compound of formula (I), wherein $R_1$ is as previously specified.

The compound of formula (II) may be synthesized similarly via a second amidation reaction between the compound of formula (VI) and a proper amine of formula (VIII)

$$H_2N-R_3,$$ (VIII)

wherein $R_3$ is as previously described.

The second amidation reaction may be performed in a solvent such as tetrahydrofuran, benzene, xylene, dimethylformamide, ethyl acetate, diethyl ether, acetonitrile, dimethyl sulfoxide, methylene chloride, chloroform, nitrobenzene, isopropanol, and mixtures thereof. Preferably, tetrahydrofuran is used as the solvent for the second amidation. In a preferred embodiment, a molar ratio of the amine of formula (VII) to the compound of formula (IV) is in a range of 0.9:1 to 2:1, preferably 1:1 to 1.5:1, or about 1.2:1.

Exemplary bases used herein for the second amidation include, without limitation, inorganic bases such as lithium hydroxide, sodium hydroxide, potassium hydroxide, rubidium hydroxide, and cesium hydroxide, and organic bases such as trimethylamine, trimethylamine, diisopropylethylamine (DIPEA), triisopropylamine, dimethylaminopropylamine, N-methylmorpholine, N-methylpyrrolidine, 4-dimethylaminopyridine (DMAP), 1,8-diazabicyclo[5.4.0]undec-7-ene (DBU), and mixtures thereof. Preferably, an inorganic base is used herein for the second amidation. More preferably, lithium hydroxide is used as the base. In one embodiment, a molar ratio of the base to the compound of formula (IV) is in a range of 1:1 to 6:1, preferably 2:1 to 5:1, more preferably 3:1 to 4:1.

A coupling reagent may be added to the reaction mixture of the carboxylate salt and the amine of formula (VII) to facilitate the second amidation reaction. Preferably, the coupling reagent is a phosphorus-based coupling reagent. Exemplary phosphorus-based coupling reagents include, but are not limited to, propylphosphonic anhydride (T3P®), diphenylphosphorazidate (DPPA), diethyl-2-(3-oxo-2,3-dihydro-1,2-benzisosulfonazolyl)phosphonate (DEBP), N,N'-bismorpholinophosphonic chloride (BMPCl), 1-oxo-chlorophospholane (CptCl), 3-(diethoxyphosphoryloxy)-1,2,3-benzotriazin-4(3H)-one diethyl tartarate (DEPBT), phosphoric acid 3,5-dioxo-10-oxa-4-azatricyclo[5.2.1.0]dec-8-en-4-yl ester diphenyl ester (ENDPP), norborn-5-ene-2,3-dicarboximidodiphenylphosphate (NDPP), and bis(2-oxooxazolidin-3-yl)phosphinic chloride (BopCl). In a preferred embodiment, T3P® is used herein as the coupling reagent. Alternatively, the coupling reagents and additives described previously for the first amidation reaction may be used in addition to, or in lieu of the phosphorus-based coupling reagent.

In one embodiment, a molar ratio of the phosphorus-based coupling reagent to the amine of formula (VII) is in a range of 4:1 to 20:1, preferably 6:1 to 16:1, preferably 8:1 to 12:1, or about 10:1. Preferably, the phosphorus-based coupling reagent may be introduced to the second amidation reaction in a two-stage or multi-stage fashion. Alternatively, the phosphorus-based coupling reagent may be introduced to the reaction mixture in one batch. In one or more embodiments, the second amidation reaction is performed at a temperature of 4-40° C., preferably 10-30° C., preferably 15-25° C. under agitation. The second amidation reaction may be conducted in inert gas (e.g. nitrogen, argon, helium). Also, in some embodiments, the reaction may not be conducted in inert gas, but in a vacuum.

The compound of formulae (I) and (II) may be isolated and purified by methods known to those of ordinary skill in the art, such as crystallization, filtration through a celite containing cartridge, evaporating the reaction mixture to dryness, aqueous work-up, extraction with organic solvents, distillation, column chromatography, and high pressure liquid chromatography (HPLC) on normal phase or reversed phase. Preferred methods include column chromatography and recrystallization.

Drug research and development efforts made by global research institutions and pharmaceutical industries have been focused on other HCV targets rather than NS4A. NS4A binding pocket remained an under-explored target for discovering new antiviral agents, which may possibly overcome emerging resistance against available drugs. Structurally, NS4A is a small peptide with 54 amino acids, which are inclined of forming proper assembly with other viral proteins. For instance, the hydrophobic N-terminal initiates a sandwich-filling binding that brings the N-terminal ($A_0$ and $A_1$ sheets) of the NS3 to rearrange and conform properly. This process is critical for the enzyme's catalytic site to attain a suitable shape that accommodates the peptide substrate [De Francesco, R.; Tomei, L.; Altamura, S.; Summa, V.; Migliaccio, G., Approaching a new era for hepatitis C virus therapy: inhibitors of the NS3-4A serine protease and the NS5B RNA-dependent RNA polymerase. *Antiviral Res* 2003, 58 (1), 1-16; Ishido, S.; Fujita, T.; Hotta, H., Complex formation of NS5B with NS3 and NS4A proteins of hepatitis C virus. *Biochemical and biophysical research communications* 1998, 244 (1), 35-40; Failla, C.; Tomei, L.; De Francesco, R., Both NS3 and NS4A are required for proteolytic processing of hepatitis C virus nonstructural proteins. *Journal of virology* 1994, 68 (6), 3753-3760; and Hamad, H. A.; Thurston, J.; Teague, T.; Ackad, E.; Yousef, M. S., The NS4A cofactor dependent enhancement of HCV NS3 protease activity correlates with a 4D geometrical measure of the catalytic triad region. *PloS one* 2016, 11 (12), e0168002]. It was found that the central part of NS4A (Gy21-Leu34) with only 14 amino acids is required for the activation of NS3 protease. Shimizu et al. observed inhibition of the enzyme via mutating the basic Arg-28 residue to a neutral glutamine (Gln) [Shimizu, Y.; Yamaji, K.; Masuho, Y.; Yokota, T.; Inoue, H.; Sudo, K.; Satoh, S.; Shimotohno, K., Identification of the sequence on NS4A required for enhanced cleavage of the NS5A/5B site by hepatitis C virus NS3 protease. *Journal of virology* 1996, 70 (1), 127-132]. Other works that discussed the NS4A site inhibitors are either presumptive [De Francesco, R.; Pessi, A.; Steinkühler, C., Mechanisms of hepatitis C virus NS3 proteinase inhibitors. *Journal of viral hepatitis* 1999, 6, 23-30; and Kim, J.; Morgenstern, K.; Lin, C.; Fox, T.; Dwyer, M.; Landro, J.; Chambers, S.; Markland, W.; Lepre, C.; O'malley, E., Crystal structure of the hepatitis C virus NS3 protease domain complexed with a synthetic NS4A cofactor peptide. *Cell* 1996, 87 (2), 343-355] or virtual (i.e. computational modeling) [Hamad, H. A.; Thurston, J.; Teague, T.; Ackad, E.; Yousef, M. S., The NS4A cofactor dependent enhancement of HCV NS3 protease activity correlates with a 4D geometrical measure of the catalytic triad region. *PloS one* 2016, 11 (12), e0168002]. As a result, non-peptide competitors of NS4A central part may be viable therapeutic options in DAA class of HCV therapeutics.

After careful inspection of 3D-visualization of crystal structures of NS4A in bound form, it was found that it forms a β-sheet that is mostly extended except a turn featuring a nearly planar area composed of an eclipsed cis bond and four trans bonds with the backbone that span through Val-26 to Arg-28. This turn is facilitated by the presence of the Gly-27 due to its small size (no side chains) (see FIG. 1). Accordingly, the compounds of formulae (I) and (II) disclosed herein are proposed via a De novo structure-based design by deriving the planar area into imidazole nucleus. Similar imidazole cores are found in several commercialized drugs such as nitronidazole (antimicrobial), azathioprine (immunosuppressive), nilotinib (anticancer), and many others [Zhang, L.; Peng, X. M.; Damu, G. L.; Geng, R. X.; Zhou, C. H., Comprehensive review in current developments of imidazole-based medicinal chemistry. *Med Res Rev* 2014, 34 (2), 340-437].

According to a third aspect, the present disclosure relates to a pharmaceutical composition involving the compound of formula (I) of the first aspect and a pharmaceutically acceptable carrier and/or excipient.

In one or more embodiments, the compound of formula (I) is

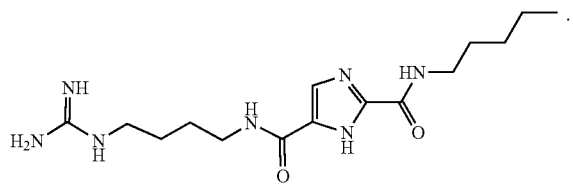 [SMILES: CCCCCNC(=O)c1ncc(C(=O)NCCCCNC(=N)N)[nH]1]

In certain embodiments, the compound of formula (II) is present in addition to, or in lieu of the compound of formula (I) in the pharmaceutical composition.

As used herein, a "composition" or a "pharmaceutical composition" refers to a mixture of the active ingredient with other chemical components, such as pharmaceutically acceptable carriers and excipients. One purpose of a composition is to facilitate administration of the compound disclosed herein in any of its embodiments to a subject. Pharmaceutical compositions of the present disclosure may be manufactured by processes well known in the art, e.g., by means of conventional mixing, dissolving, granulating, dragee-making, levigating, emulsifying, encapsulating, entrapping or lyophilizing processes. Depending on the intended mode of administration (oral, parenteral, or topical), the composition can be in the form of solid, semi-solid or liquid dosage forms, such as tablets, suppositories, pills, capsules, powders, liquids, or suspensions, preferably in unit dosage form suitable for single administration of a precise dosage.

The term "active ingredient", as used herein, refers to an ingredient in the composition that is biologically active, for example, the compound represented by formula (I), the compound represented by formula (II), a salt thereof, a solvate thereof, a tautomer thereof, a stereoisomer thereof, or any mixtures thereof. In some embodiments, other active ingredients in addition to the compound of the current disclosure may be incorporated into a pharmaceutical composition.

In one or more embodiments, the pharmaceutical composition disclosed herein further includes an antiviral agent that is structurally distinct from the compounds of formulae (I) and (II). In one embodiment, the antiviral agent used herein does not have anti-HCV activity. Preferably, the antiviral agent has anti-HCV activity. As used herein, the term "anti-HCV activity" means the agent is effective to inhibit the function of at least one target selected from the group consisting of HCV metalloprotease, HCV serine protease, HCV polymerase, HCV helicase, HCV NS4B protein, HCV entry, HCV assembly, HCV egress, HCV NS5A protein, IMPDH and a nucleoside analog for the treatment of an HCV infection. In one embodiment, the antiviral agent having anti-HCV activity is effective to inhibit the function of a target in the HCV life cycle other than the HCV serine protease.

Exemplary antiviral agents with anti-HCV activity include, but are not limited to, Imiqimod, ribavirin, amantadine, rimantadine, interferon such as interferon alpha 213, pegylated interferon alpha, consensus interferon, interferon alpha 2A, and lymphoblastiod interferon tau, interleukins such as interleukin 2, interleukin 6, and interleukin 12, other inhibitors of HCV NS3 protease, inhibitors of other targets in the HCV life cycle such as helicase, polymerase, metalloprotease, or internal ribosome entry site; or combinations thereof, and the like. Other antiviral agents such as oseltamivir (Tamiflu), zanamivir, peramivir (Rapivab®) may be further combined into the pharmaceutical composition for the prevention or treatment of secondary infection. Alternatively, the antiviral agent may act as an additional therapy, and the compounds of formula (I) and/or (II) may be administered with the antiviral agent in combination therapy, either jointly or separately.

In one or more embodiments, the pharmaceutical composition comprises up to 0.01%, up to 0.1%, up to 1%, up to 5%, or up to 10% by weight of the pharmaceutically acceptable carrier and/or excipient relative to a total weight of the pharmaceutical composition. In one or more embodiments, the pharmaceutical composition comprises at least 0.01 wt %, at least 0.05 wt %, at least 0.1 wt %, at least 0.5 wt %, at least 5 wt %, at least 10 wt %, at least 15 wt %, at least 20 wt %, at least 25 wt %, at least 30 wt %, at least 35 wt %, at least 40 wt %, at least 45 wt %, at least 50 wt %, at least 55 wt %, at least 60 wt %, at least 65 wt %, at least 70 wt %, at least 75 wt %, at least 80 wt %, at least 85 wt %, at least 90 wt %, at least 95 wt %, at least 99 wt %, or at least 99.9 wt % of the compound of formula (I) relative to a total weight of the pharmaceutical composition. The pharmaceutical composition may contain 0.5-500 μM of the compound of formula (I) relative to a total volume of the composition, preferably 1-400 μM, preferably 10-300 μM, preferably 20-200 μM of the compound of formula (I) relative to the total volume of the composition. In some embodiments, the composition comprises up to 0.1 wt %, 1 wt %, 5 wt %, or 10 wt % of a pharmaceutically acceptable salt of the compound of formula (I). In some embodiments, the composition comprises up to 0.1 wt %, 1 wt %, 5 wt %, or 10 wt % of a pharmaceutically acceptable solvate of the compound of formula (I). Preferably, the composition may further comprise pharmaceutically acceptable binders, such as sucrose, lactose, xylitol, and pharmaceutically acceptable excipients such as calcium carbonate, calcium phosphate, and dimethyl sulfoxide (DMSO).

As used herein, a "pharmaceutically acceptable carrier" refers to a carrier or diluent that does not cause significant irritation to an organism, does not abrogate the biological activity and properties of the administered active ingredient, and/or does not interact in a deleterious manner with the other components of the composition in which it is contained. The term "carrier" encompasses any excipient, binder, diluent, filler, salt, buffer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g. Remington's Pharmaceutical Sciences, 21st Edition, ed. University of the Sciences in Philadelphia, Lippincott, Williams & Wilkins, Philadelphia Pa., 2005, which is incorporated herein by reference in its entirety). Examples of physiologically acceptable carriers include antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN® (ICI, Inc.; Bridgewater, N.J.), polyethylene glycol (PEG), and PLURONICS™ (BASF; Florham Park, N.J.). An "excipient" refers to an inert substance added to a composition to further facilitate administration of a compound. Examples, without limitation, of excipients include calcium carbonate, calcium phosphate, various sugars and types of starch, cellulose derivatives, gelatin, vegetable oils, and polyethylene glycols.

In one or more embodiments, the pharmaceutically acceptable carrier and/or excipient is at least one selected from the group consisting of a buffer, an inorganic salt, a fatty acid, a vegetable oil, a synthetic fatty ester, a surfactant, and a polymer.

Exemplary buffers include, but are not limited to, phosphate buffers, citrate buffer, acetate buffers, borate buffers, carbonate buffers, bicarbonate buffers, and buffers with other organic acids and salts.

Exemplary inorganic salts include, but are not limited to, calcium carbonate, calcium phosphate, disodium hydrogen phosphate, potassium hydrogen phosphate, sodium chloride, zinc oxide, zinc sulfate, and magnesium trisilicate.

Exemplary fatty acids include, but are not limited to, an omega-3 fatty acid (e.g., linolenic acid, docosahexaenoic acid, eicosapentaenoic acid) and an omega-6 fatty acid (e.g., linoleic acid, eicosadienoic acid, arachidonic acid). Other fatty acids, such as oleic acid, palmitoleic acid, palmitic acid, stearic acid, and myristic acid, may be included.

Exemplary vegetable oils include, but are not limited to, avocado oil, olive oil, palm oil, coconut oil, rapeseed oil, soybean oil, corn oil, sunflower oil, cottonseed oil, and peanut oil, grape seed oil, hazelnut oil, linseed oil, rice bran oil, safflower oil, sesame oil, brazil nut oil, carapa oil, passion fruit oil, and cocoa butter.

Exemplary synthetic fatty esters include, without limitation, methyl, ethyl, isopropyl and butyl esters of fatty acids (e.g., isopropyl palmitate, glyceryl stearate, ethyl oleate, isopropyl myristate, isopropyl isostearate, diisopropyl sebacate, ethyl stearate, di-n-butyl adipate, dipropylene glycol pelargonate), $C_{12}$-$C_{16}$ fatty alcohol lactates (e.g., cetyl lactate and lauryl lactate), propylene dipelargonate, 2-ethylhexyl isononoate, 2-ethylhexyl stearate, isopropyl lanolate, 2-ethylhexyl salicylate, cetyl myristate, oleyl myristate, oleyl stearate, oleyl oleate, hexyl laurate, isohexyl laurate, propylene glycol fatty ester, and polyoxyethylene sorbitan fatty ester. As used herein, the term "propylene glycol fatty ester" refers to a monoether or diester, or mixtures thereof, formed between propylene glycol or polypropylene glycol and a fatty acid. The term "polyoxyethylene sorbitan fatty ester" denotes oleate esters of sorbitol and its anhydrides, typically copolymerized with ethylene oxide.

Surfactants may act as detergents, wetting agents, emulsifiers, foaming agents, and dispersants. Surfactants that may be present in the compositions of the present disclosure include zwitterionic (amphoteric) surfactants, e.g., phosphatidylcholine, and 3-[(3-cholamidopropyl)dimethylammonio]-1-propanesulfonate (CHAPS), anionic surfactants, e.g., sodium lauryl sulfate, sodium octane sulfonate, sodium decane sulfonate, and sodium dodecane sulfonate, non-ionic surfactants, e.g., sorbitan monolaurate, sorbitan monopalmitate, sorbitan trioleate, polysorbates such as polysorbate 20 (Tween 20), polysorbate 60 (Tween 60), and polysorbate 80 (Tween 80), cationic surfactants, e.g., decyltrimethylammonium bromide, dodecyltrimethylammonium bromide, tetradecyltrimethylammonium bromide, tetradecyltrimethyl-ammonium chloride, and dodecylammonium chloride, and combinations thereof.

Exemplary polymers include, without limitation, polylactides, polyglycolides, polycaprolactones, polyanhydrides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malic acid), poly(maleic anhydride), a polyvinyl alcohols, and copolymers, terpolymers, or combinations or mixtures therein. The copolymer/terpolymer may be a random copolymer/terpolymer, or a block copolymer/terpolymer.

Depending on the route of administration e.g. oral, parental, or topical, the composition may be in the form of solid dosage form such as tablets, caplets, capsules, powders, and granules, semi-solid dosage form such as ointments, creams, lotions, gels, pastes, and suppositories, liquid dosage forms such as solutions, and dispersions, inhalation dosage form such as aerosols, and spray, or transdermal dosage form such as patches.

Solid dosage forms for oral administration can include capsules, tablets, pills, powders, and granules. In such solid dosage forms, the active ingredient is ordinarily combined with one or more adjuvants appropriate to the indicated route of administration. If administered per os, the active ingredient can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering ingredients such as sodium citrate, magnesium or calcium carbonate or bicarbonate. Tablets and pills can additionally be prepared with enteric coatings.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting ingredients, emulsifying and suspending ingredients, and sweetening, flavouring, and perfuming ingredients.

For therapeutic purposes, formulations for parenteral administration can be in the form of aqueous or non-aqueous isotonic sterile injection solutions or suspensions. The term "parenteral", as used herein, includes intravenous, intravesical, intraperitoneal, subcutaneous, intramuscular, intralesional, intracranial, intrapulmonal, intracardial, intrasternal, and sublingual injections, or infusion techniques. These solutions and suspensions can be prepared from sterile powders or granules having one or more of the carriers or diluents mentioned for use in the formulations for oral administration. The active ingredient can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Injectable preparations, for example, sterile injectable aqueous or oleaginous suspensions can be formulated according to the known art using suitable dispersing or wetting ingredients and suspending ingredients. The sterile injectable preparation can also be a sterile injectable solution or suspension in a non-toxic parenterally acceptable diluent or solvent, for example, as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or di-glycerides. In addition, fatty acids, such as oleic acid, find use in the preparation of injectables. Dimethyl acetamide, surfactants including ionic and non-ionic detergents, polyethylene glycols can be used. Mixtures of solvents and wetting ingredients such as those discussed above are also useful.

Suppositories for rectal administration can be prepared by mixing the active ingredient with a suitable non-irritating excipient, such as cocoa butter, synthetic mono-, di-, or triglycerides, fatty acids, and polyethylene glycols that are solid at ordinary temperatures but liquid at the rectal temperature and will therefore melt in the rectum and release the drug.

Topical administration may involve the use of transdermal administration such as transdermal patches or iontophoresis devices. Formulation of drugs is discussed in, for example, Hoover, J. E. Remington's pharmaceutical sciences, Mack Publishing Co., Easton, Pa., 1975; and Liberman, H. A.; Lachman, L., Eds. Pharmaceutical dosage forms, Marcel Decker, New York, N.Y., 1980, which are incorporated herein by reference in their entirety.

In other embodiments, the pharmaceutical composition having the compound of formula (I), the salt thereof, the solvate thereof, the tautomer thereof, the stereoisomer thereof, or the mixture thereof has different release rates categorized as immediate release and controlled- or sustained-release.

As used herein, immediate release refers to the release of an active ingredient substantially immediately upon administration. In another embodiment, immediate release occurs when there is dissolution of an active ingredient within 1-20 minutes after administration. Dissolution can be of all or less than all (e.g. about 70%, about 75%, about 80%, about 85%, about 90%, about 91%, about 92%, about 93%, about 94%, about 95%, about 96%, about 97%, about 98%, about 99%, about 99.5%, 99.9%, or 99.99%) of the active ingredient. In another embodiment, immediate release results in complete or less than complete dissolution within about 1 hour following administration. Dissolution can be in a subject's stomach and/or intestine. In one embodiment, immediate release results in dissolution of an active ingredient within 1-20 minutes after entering the stomach. For example, dissolution of 100% of an active ingredient can occur in the prescribed time. In another embodiment, immediate release results in complete or less than complete dissolution within about 1 hour following rectal administration. In some embodiments, immediate release is through inhalation, such that dissolution occurs in a subject's lungs.

Controlled-release, or sustained-release, refers to a release of an active ingredient from a composition or dosage form in which the active ingredient is released over an extended period of time. In one embodiment, controlled-release results in dissolution of an active ingredient within 20-180 minutes after entering the stomach. In another embodiment, controlled-release occurs when there is dissolution of an active ingredient within 20-180 minutes after being swallowed. In another embodiment, controlled-release occurs when there is dissolution of an active ingredient within 20-180 minutes after entering the intestine. In another embodiment, controlled-release results in substantially complete dissolution after at least 1 hour following administration. In another embodiment, controlled-release results in substantially complete dissolution after at least 1 hour following oral administration. In another embodiment, controlled-release results in substantially complete dissolution after at least 1 hour following rectal administration. In one embodiment, the pharmaceutical composition described herein is not a controlled-release composition.

According to a fourth aspect, the present disclosure relates to a method of preventing or treating hepatitis C virus (HCV) infection. The method involves administering the pharmaceutical composition of the third aspect to a subject in need of therapy.

As used herein, the term "preventing" in the context of the administration of a therapy to a subject in need thereof refers to preventing a disease, disorder or condition from occurring in a subject which may be predisposed to the disease, disorder and/or condition but has not yet been diagnosed as having it. The term "treating" refers to (i) inhibiting the disease, disorder or condition, i.e., arresting its development; and (ii) relieving the disease, disorder or condition, i.e., causing regression of the disease, disorder and/or condition. Treatment is preferably commenced at the time of infection or post infection with HCV. It is recommended that the treatment continues until the virus is no longer present or active. For protecting a non-infected subject from future infection, the treatment continues for as long as there is a potential exposure to the virus.

The term "subject" and "patient" are used interchangeably. As used herein, they refer to any subject for whom or which therapy, including with the compositions according to the present disclosure is desired. In most embodiments, the subject is a mammal, including but not limited to a human, a non-human primate such as a chimpanzee, a domestic livestock such as a cattle, a horse, a swine, a pet animal such as a dog, a cat, and a rabbit, and a laboratory subject such as a rodent, e.g. a rat, a mouse, and a guinea pig. In preferred embodiments, the subject is a human.

The terms "administer", "administering", "administration", and the like, as used herein, refer to the methods that may be used to enable delivery of the active ingredient and/or the composition to the desired site of biological action. Routes or modes of administration are as set forth herein. These methods include, but are not limited to, oral routes, intraduodenal routes, parenteral injection (including intravenous, subcutaneous, intraperitoneal, intramuscular, intravascular, or infusion), topical and rectal administration. Those of ordinary skill in the art are familiar with administration techniques that can be employed with the compounds and methods described herein. In a preferred embodiment, the active ingredient and/or the pharmaceutical composition described herein are administered orally.

In one or more embodiments, the pharmaceutical composition administered comprises the compound of formula (I), or a salt thereof, a solvate thereof, a tautomer thereof, a stereoisomer thereof, or a mixture thereof. In a preferred embodiment, the pharmaceutical composition administered comprises a compound which is

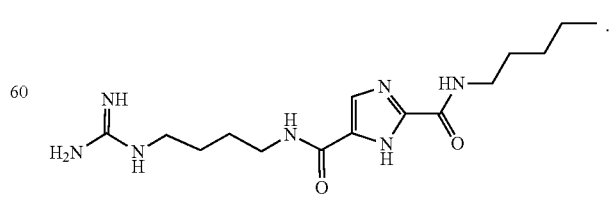

The dosage amount and treatment duration are dependent on factors, such as bioavailability of a drug, administration mode, toxicity of a drug, gender, age, lifestyle, body weight, the use of other drugs and dietary supplements, the disease stage, tolerance and resistance of the body to the administered drug, etc., and then determined and adjusted accordingly. The terms "effective amount", "therapeutically effective amount", or "pharmaceutically effective amount" refer to that amount of the active ingredient being administered which will relieve to some extent one or more of the symptoms of the disease being treated. The result can be a reduction and/or alleviation of the signs, symptoms, or causes of a disease, or any other desired alteration of a biological system. An appropriate "effective amount" may differ from one individual to another. An appropriate "effective amount" in any individual case may be determined using techniques, such as a dose escalation study. In one or more embodiments, an effective amount of the compound of formula (I) in a range of 0.1-100 mg/kg, preferably 0.5-50 mg/kg, more preferably 1-25 mg/kg is administered per body weight of the subject. However, in certain embodiments, the effective amount of the compound of formula (I) is less than 0.1 mg/kg or greater than 100 mg/kg. In general, the compound is most desirably administered at a concentration level that will generally afford antivirally effective results without causing any harmful or deleterious side effects.

A treatment method may comprise administering a pharmaceutical composition containing the compound of formula (I) of the current disclosure in any of its embodiments as a single dose or multiple individual divided doses. In some embodiments, the interval of time between the administration of the composition and the administration of one or more additional therapies (e.g. interferon, ribavirin) may be about 1-5 minutes, 1-30 minutes, 30 minutes to 60 minutes, 1 hour, 1-2 hours, 2-6 hours, 2-12 hours, 12-24 hours, 1-2 days, 2 days, 3 days, 4 days, 5 days, 6 days, 7 days, 1 week, 2 weeks, 3 weeks, 4 weeks, 5 weeks, 6 weeks, 7 weeks, 8 weeks, 9 weeks, 10 weeks, 15 weeks, 20 weeks, 26 weeks, 52 weeks, 11-15 weeks, 15-20 weeks, 20-30 weeks, 30-40 weeks, 40-50 weeks, 1 month, 2 months, 3 months, 4 months, 5 months, 6 months, 7 months, 8 months, 9 months, 10 months, 11 months, 12 months, 1 year, 2 years, or any period of time in between. Preferably, the pharmaceutical compositions disclosed herein will be administered from about 1 to about 5 times per day or alternatively, as a continuous infusion for at least 2 days, at least 5 days, at least 6 days, or at least 7 days. Such administration can be used as a chronic or acute therapy. In certain embodiments, the composition and one or more additional therapies are administered less than 1 day, less than 1 week, less than 2 weeks, less than 3 weeks, less than 4 weeks, less than 1 month, less than 2 months, less than 3 months, less than 6 months, less than 1 year, less than 2 years, or less than 5 years apart.

The pharmaceutical composition may be administered in vivo to the subject to inhibit HCV NS3 protease or to treat or prevent HCV virus infection. In one or more embodiments, the compound of formula (I) of the current disclosure in any of its embodiments binds to an activation site of hepatitis C virus (HCV) serine protease. As used herein, the "serine protease" is referred to as NS3 protease. The compound of formula (I) may preferably bind to the activation site of HCV NS3 protease such as but not limited to linear peptides, cyclic peptides, macrolactons, macrolactams, and peptidomimetics. In a preferred embodiment, the compound of formula (I) of the current disclosure in any of its embodiments binds to NS3/4A serine protease.

As used herein, "bind" or "binding" refers to a process involving an active ingredient (e.g. the compound of formula (I)) reversibly or irreversibly binds to HCV NS3 protease or variant thereof at the activation site. Binding may involve the formation of bonds which may be covalent or non-covalent. Non-covalent bonds may be e.g. hydrogen bonds, ionic bonds, or hydrophobic interactions. The active ingredient (e.g. the compound of formula (I)) is expected to interfere and inhibit the interactions leading to the formation of the active form of the NS3 protease. Binding can be quantitated in accordance with methods well-known in the art and described herein below.

In certain embodiments, a suitable assay is used to characterize the potential binding ability of the active ingredient (e.g. compound of formula (I)) to bind to the activation site. This may involve directly testing the active ingredient's ability to bind, and/or determining whether the active ingredient has an influence on the binding of the NS4A to HCV NS3 protease or variants thereof. To evaluate binding properties of binding compounds, assays may be used. Exemplary assay methods include, but not limited to, calorimetric techniques, surface plasmon resonance (SPR), and spectroscopic methods such as NMR, fluorescence, and UV-vis spectroscopies.

Calorimetric methods include but not limited to isothermal titration calorimetry and differential scanning calorimetry. SPR is the resonant oscillation of conduction electrons at the interface between negative and positive permittivity material stimulated by incident light. The method involves immobilizing one molecule of a binding pair on the sensor chip surface ("ligand", in Biacore parlance) and injecting a series of concentrations of its partner ("analyte") across the surface. Changes in the index of refraction at the surface where the binding interaction occurs are detected by the hardware and recorded as RU (resonance units) in the control software. Curves are generated from the RU trace and are evaluated by fitting algorithms which compare the raw data to well-defined binding models. These fits allow determination of a variety of thermodynamic constants, including the apparent affinity of the binding interaction. SPR main advantage is that it does not require labeling the protein or the binding compound.

The kinetics of enzymatic-catalyzed reactions is a useful tool not only to determine the inhibition constants (Ki) for an inhibitor but also the site at which an inhibitor binds to the enzyme. An inhibitor that binds exclusively to the catalytic active site displays a competitive inhibition pattern with the substrate. In contrast, an inhibitor that binds to a different site from that of the substrate displays an uncompetitive inhibition pattern with the substrate. If the inhibitor binds to both an active site and a different site from that of the active site, it would display a non-competitive pattern. Thus, the active ingredient (e.g. the compound of formula (I)) would be competitive with the activation peptide and uncompetitive with the substrate.

NMR methods and optical spectroscopic methods such as fluorescence (e.g. fluorescence anisotropy (FA)), UV-vis, and circular dichroism (CD) are well-known assays utilized in measuring the kinetics of the interaction between an active ingredient and a protein. In a preferred embodiment, fluorescence anisotropy is used.

Figure 5:
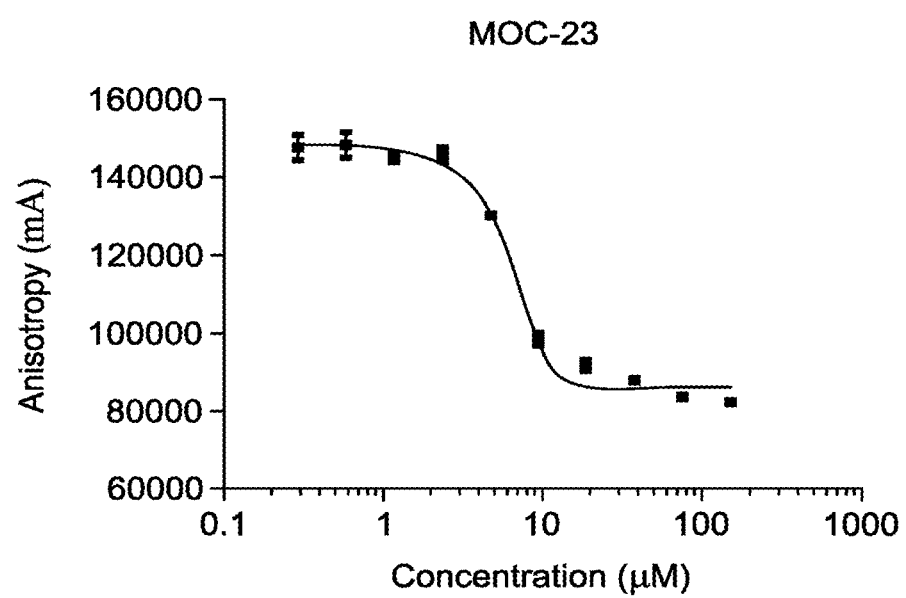
FIG. 5 shows a competition assay using fluorescence anisotropy that determines ability of compounds of formula (I) replacing FITC-NS4A in binding with NS3.
Figure 6:
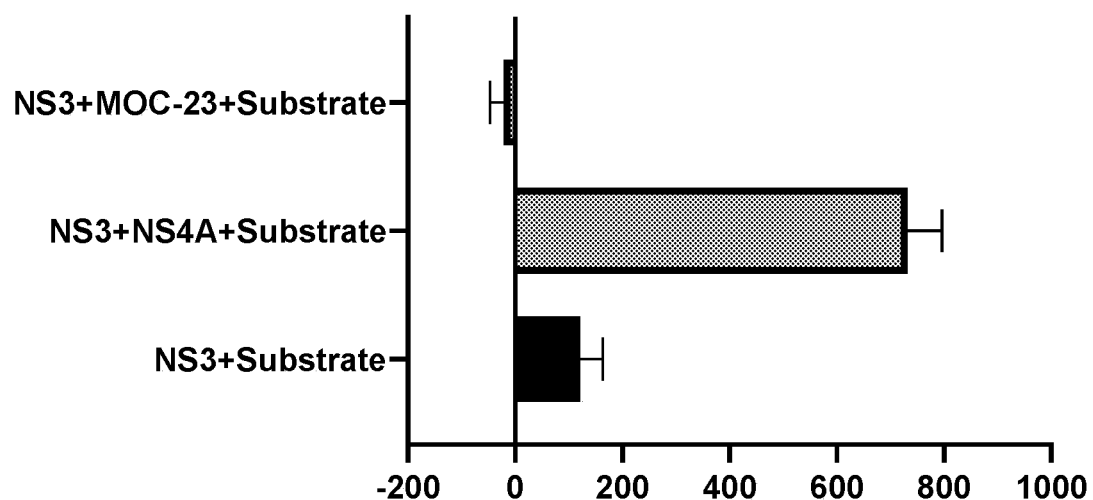
FIG. 6 is an enzyme inhibition assay that shows the effect of compound MOC-23 on NS3 activity.

The fluorescence method is suitable for high throughput screening method amenable to automation in a laboratory environment. Since HCV NS3 contains two tryptophan residues and four tyrosine residues, the binding of an inhibitor (e.g. the compound of formula (I), NS4A) to the activation site may be accompanied by significant change in the intrinsic fluorescence of the protein, and hence the enzyme inhibition may be evaluated (see FIG. 6). A peptide inhibitor (e.g. NS4A) may be labeled with a fluorescent probe and the binding of the labeled peptide to the enzyme is accompanied by fluorescent change (see Example 12, 13, FIG. 6). Another fluorescence assay method for determining the binding constant of the compound of formula (I) disclosed herein is a competitive displacement assay (see Examples 11, 13, FIG. 5).

NMR methods may be used to observe the binding of an active ingredient (e.g. the compound of formula (I)) to the activation site of HCV NS3 protease. In its simple form, the observation of broadening of an NMR signal as a function of concentration would allow the determination of binding constants.

The examples below are intended to further illustrate protocols for preparing, characterizing the compound of formulae (I) and (II), and uses thereof, and are not intended to limit the scope of the claims.

Example 1

Synthesis of Screened Compounds

The compounds were synthesized using straightforward chemistry [Duguay, G.; Guémas, J.-P.; Meslin, J.-C.; Pradere, J.-P.; Reliquet, F.; Reliquet, A.; Tea-Gokou, C.; Quiniou, H.; Rabiller, C., Heteroatomic chains and their products of cyclisation. IV. t-butyl-2-phthalimido-2-(3,6-dihydro-1,3-2H-thiazine-2-yliden)-acetates substituted in position 5 by a functional group. *Journal of Heterocyclic Chemistry* 1980, 17 (4), 767-770; and Vuilhorgne, M.; Malpart, J.; Mutti, S.; Mignani, S., Preparative route to 2-ethoxycarbonylimidazole-4-phosphonate and diethylimidazole-2,4-dicarboxylate. *Journal of Heterocyclic Chemistry* 2003, 40 (1), 159-162, each incorporated herein by reference in their entirety] as illustrated in the synthesis scheme (FIG. 2). All final compounds are new and their structures were confirmed by spectral analyses (e.g. $^1$H NMR, $^{13}$C NMR, and LC/MS).

Example 2

Chemical Synthesis: General

Solvents and reagents were purchased from Sigma-Aldrich (USA), VWR (USA) or Alfa Aesar (UK). When needed, solvents were dried according procedures described in literature. Unless stated otherwise, reactions were performed under inert atmosphere of nitrogen. Melting points (m.p.) were determined in open capillary tubes using Electrothermal apparatus (Stuart, UK) and were uncorrected. NMR spectra were recorded on Bruker DPX-300 MHz (Bruker, Switzerland). HPLC-Mass Spectrometry was performed on Agilent 1100/ZQ MSD including diod-array UV detector.

Example 3

Synthesis of 5-(tert-butyl) 2-ethyl 1H-imidazole-2,5-dicarboxylate (MOC-01)

Water (0.6 mL/mmol) was added dropwise over a period of 2 h to a stirred mixture of ethyl cyanoformate (1.0 equiv, 3 g, 30.3 mmol), hydroxylamine hydrochloride (1.5 equiv, 3.16 g, 45.45 mmol), and sodium carbonate (0.77 equiv, 2.47 g, 23.331 mmol) in ethanol (1 mL/mmol) at r.t. Upon completion, the reaction was quenched and the solvent was removed under vacuum. The resulting residue was extracted with DCM, and the combined organic layers were washed with brine, dried over $MgSO_4$, filtered, and concentrated to afford a white solid. The intermediate (Z)-2-amino-2-(hydroxyimino) acetate was recrystallized from chloroform and n-heptane to afford white crystals (1.88 g, 47%). This intermediate (1.0 equiv, 132 mg, 1 mmol) was added to a solution of tBu-propiolate (1.0 equiv, 126 mg, 1 mmol), $Et_3N$ (1.0 equiv, 101 mg, 1 mmol) and toluene (5.5 mL/mmol). The resulting solution was MW irradiated at 120° C. for 3 min (300 W) and then for an additional 10 min. The solvent was evaporated and the final product was purified via preparative HPLC. $^1$H NMR (300 MHz, DMSO-$d_6$) $d_H$ ppm 13.72 (br., 1H), 7.87 (s, 1H), 4.34 (q, J=7.18 Hz, 2H), 1.51 (s, 9H), 1.32 (t, J=6.99 Hz, 3H); $^{13}$C NMR (214 MHz, $CDCl_3$) $d_c$ 169.7, 136.5, 129.5, 129.1, 128.9, 127.8, 123.8, 29.7; IR (FT-IR, $cm^{-1}$): 3025.37, 2916.82, 2843.61, 1695.04, 1619.31, 1594.07, 1571.35, 1505.72, 1445.14, 1399.70, 1359.31, 1270.96, 1205.32; LC-MS (ESI), RT=1.41 min, m/z 241.3 $[M+H]^+$.

Example 4

Synthesis of 2-(ethoxycarbonyl)-1H-imidazole-4-carboxylic acid (MOC-02)

A solution of 5-tert-butyl 2-ethyl 1H-imidazole-2,5-dicarboxylate (1 equiv, 4.299 g, 17.6 mmol) and $CF_3COOH$ (1.2 mL/mmol) in DCM (0.84 mL/mmol) was stirred for 12 h at r.t. The solvent was evaporated under vacuum and the remaining residue was treated with MeOH (4 mL/mmol) and filtered to give a yellow solid (2.841 g, 86.29%). $^1$H NMR (300 MHz, DMSO-$d_6$) $d_H$ ppm 13.72 (br. s, 1H); 12.59 (br. s, 1H), 7.91 (s, 1H), 4.33 (q, J=6.97 Hz, 2H), 1.32 (t, J=7.06 Hz, 3H); LC-MS (ESI), RT=1.55 min, m/z 185.3 $[M+H]^+$.

Example 5

General Procedure for the Synthesis of ethyl 4-(N-substitutedcarbamoyl)-1H-imidazole-2-carboxylate (MOC-03 to MOC-6)

Under inert atmosphere, the carboxylic acid MOC-02 (1.0 equiv., 5.21 mmol) was dissolved in dry THF (5 mL/mmol) then EDCI (1.0 equiv, 0.998 g, 5.21 mmol), HOBt (1.0 equiv, 0.704 mg, 5.21 mmol), DIPEA (1.5 equiv, 1.01 g, 7.8 mmol), and the amine (1.2 equiv, 6.252 mmol) were added orderly. The mixture was stirred at r.t. for 1 h then heated to 60° C. After 3 h, EDCI (0.5 equiv, 0.5 g, 2.6 mmol), HOBt (0.5 equiv, 0.352 g, 2.6 mmol), DIPEA (0.75 equiv, 0.505 g, 3.9 mmol) were added to the mixture. After completion, the mixture was purified by column chromatography using 50-100% EtOAc in cyclohexane.

Ethyl 4-((2-(methylamino)-2-oxoethyl)carbamoyl)-1H-imidazole-2-carboxylate (MOC-03)

Yield was 77%. $^1$H NMR (300 MHz, DMSO-$d_6$) $d_H$ ppm 8.19 (br. s., 1H), 7.81 (s, 2H), 4.35 (q, J=7.16 Hz, 2H), 3.81 (d, J=5.65 Hz, 2H), 2.59 (d, J=4.52 Hz, 3H), 1.33 (t, J=7.16 Hz, 3H); LC-MS (ESI), RT=1.57 min, m/z 255.3 $[M+H]^+$.

Synthesis of (((4-aminobutyl)amino)(carboxyamino) methylene)carbamic acid ditert-butyl ester (Amine Reactant for MOC-04)

To a solution of 1,4-diaminobutane (2.0 equiv, 303.24 mg, 3.44 mmol) in THF (1.3 mL/mmol), a solution of 1,3-bis (tert-butoxycarbonyl)-2-methyl-2-thiopseudourea (1.0 equiv, 500 mg, 1.72 mmol) in THF (1.7 mL/mmol) was added within 0.5 h. The solution was stirred at room temperature for 1 h. After completion, the solvent was removed under vacuum and the product was purified by column chromatography on silica gel using a mixture of DCM/MeOH to give (((4-aminobutyl)amino)(carboxyamino)methylene)carbamic acid ditert-butyl ester (250 mg, 52.88%); $^1$H NMR (300 MHz, CDCl$_3$) d$_H$ ppm 11.51 (br. s., 1H), 8.36 (br. s., 1H), 3.40-3.52 (m, 2H), 2.75 (t, J=6.69 Hz, 2H), 1.51-1.71 (m, 4H), 1.52 (s, 9H), 1.51 (s, 9H); LC-MS (ESI), RT=2.44 min, m/z 331.8 [M+H]$^+$.

Ethyl (E)-4-((4-(2,3-bis(tert-butoxycarbonyl)guanidino)butyl)carbamoyl)-1H-imidazole-2-carboxylate (MC-04)

Yield was 36%. The compound was used as the starting material for the next step without further characterization.

Ethyl 5-((pyridin-2-ylmethyl)carbamoyl)-1H-imidazole-2-carboxylate (MOC-05)

Yield was 94%. $^1$H NMR (300 MHz, DMSO-d$_6$) d$_H$ ppm 13.24 (br. s. 1H), 8.69 (t, J=5.65 Hz, 1H), 8.51 (d, J=4.14 Hz, 1H), 8.41 (s, 1H), 7.81 (s, 1H), 7.74 (t, J=7.06 Hz, 1H), 7.19-7.35 (m, 2H), 4.53 (d, J=6.03 Hz, 2H), 4.34 (q, J=7.16 Hz, 2H), 1.32 (t, J=7.06 Hz, 3H); LC-MS (ESI), RT=1.14 min, m/z 275.3 [M+H]$^+$.

Ethyl 5-((furan-2-ylmethyl)carbamoyl)-1H-imidazole-2-carboxylate (MOC-06)

Yield was 76%. $^1$H NMR (300 MHz, DMSO-d$_6$) d$_H$ ppm 13.76 (br. s., 1H), 8.53 (br. s., 1H), 7.82 (s, 1H), 7.50-7.58 (m, 1H), 6.22 (d, J=3.02 Hz, 1H), 6.38 (dd, J=3.02, 1.89 Hz, 1H), 6.22 (d, J=3.02 Hz, 1H), 4.41 (d, J=6.04 Hz, 2H), 4.34 (q, J=7.18 Hz, 2H), 1.32 (t, J=6.99 Hz, 3H).

Example 6

General Procedure for the Synthesis of MOC-07 to MOC-10
The ethyl esters (1.0 equiv) was dissolved in TH/water 4:1 (4 mL/mmol) then LiOH (3.0 equiv) was added. The mixture was stirred at r.t. until completion. Afterwards, the solvent was evaporated under vacuum. The remaining residue was re-suspended in EtOH/toluene and evaporated. No further purification or characterization was performed and the salts were used for the next step.

Example 7

General Procedure for the Synthesis of MOC-11 to MOC-36
Under inert atmosphere, the appropriate lithium salt imidazole-carboxylic acid derivative of MOC-7 to MOC-10 (1.0 equiv.) was dissolved in dry THF (3 mL/mmol) then propanephosphonic acid anhydride (T$_3$P, 50% solution in THF, 6.0 equiv.) and the requisite amine derivative (1.2 equiv.) were added. The mixture was stirred at r.t. for 72 h. After 24 h, 6.0 equiv. of T$_3$P (50% solution in THF) was added to the mixture. Upon reaction completion, the solvent was evaporated and the residue was purified on a silica gel column with 0-20% MeOH in CDCl$_3$, and then the crude product was collected and purified by prep HPLC.

N$^5$-(2-(methylamino)-2-oxoethyl)-N$^2$-(n-pentyl)-1H-imidazole-2,5-dicarboxamide (MOC-11)

$^1$H NMR (300 MHz, METHANOL-d$_4$) d$_H$ ppm 7.76 (s, 1H), 4.04 (s, 1H), 3.74 (t, J=6.42 Hz, 2H), 3.38-3.51 (m, 1H), 2.78 (s, 2H), 1.80-2.00 (m, 2H), 1.53-1.80 (m, 2H), 1.20-1.53 (m, 3H), 0.86-1.07 (m, 3H); $^{13}$C NMR (75 MHz, METHANOL-d$_4$) d$_C$ ppm 170.8, 48.5, 48.2, 47.9, 47.6, 47.4, 47.1, 46.8, 41.8, 38.9, 29.0, 28.9, 25.0, 22.1, 13.0; LC-MS (ESI), RT=1.46 min, m/z 296.4 [M+H]$^+$.

N$^2$-(n-hexyl)-N$^5$-(2-(methylamino)-2-oxoethyl)-1H-imidazole-2,5-dicarboxamide (MOC-12)

$^1$H NMR (300 MHz, METHANOL-d$_4$) d$_H$ ppm 7.76 (s, 1H), 4.04 (s, 1H), 3.39 (t, J=7.18 Hz, 1H), 2.78 (s, 2H), 1.56-1.91 (m, 3H), 1.38 (br. s., 5H), 1.04 (t, J=6.42 Hz, 2H), 0.77-0.98 (m, 3H); $^{13}$C NMR (75 MHz, METHANOL-d$_4$) d$_C$ ppm 48.5, 48.2, 47.9, 47.6, 47.4, 47.1, 46.8, 41.8, 39.0, 31.3, 29.2, 26.3, 25.0, 22.3, 13.0; LC-MS (ESI), RT=1.39 min, m/z 310.3 [M+H]$^+$.

N$^2$-(n-heptyl)-N$^5$-(2-(methylamino)-2-oxoethyl)-1H-imidazole-2,5-dicarboxamide (MOC-13)

$^1$H NMR (300 MHz, METHANOL-d$_4$) d$_H$ ppm 7.68 (s, 1H), 3.95 (s, 2H), 2.69 (s, 3H), 1.45-1.73 (m, 2H), 1.25 (s, 5H), 1.29 (s, 4H), 0.63-1.01 (m, 4H); $^{13}$C NMR (75 MHz, METHANOL-d$_4$) d$_C$ ppm 48.5, 48.2, 47.9, 47.6, 47.4, 47.1, 46.8, 38.9, 31.6, 29.3, 28.8, 26.6, 25.0, 22.3, 13.0; LC-MS (ESI), RT=2.59 min, m/z 324.4 [M+H]$^+$.

N$^2$-(2-(cyclohexyloxy)ethyl)-N$^5$-(2-(methylamino)-2-oxoethyl)-1H-imidazole-2,5-dicarboxamide (MOC-14)

$^1$H NMR (300 MHz, METHANOL-d$_4$) d$_H$ ppm 7.77 (s, 1H), 3.84-4.24 (m, 2H), 3.66 (t, J=5.48 Hz, 2H), 3.56 (t, J=5.29 Hz, 2H), 2.77 (s, 3H), 1.93 (br. s., 2H), 1.62-1.84 (m, 4H), 1.45-1.62 (m, 1H), 1.16-1.41 (m, 6H), 0.98-1.12 (m, 1H); $^{13}$C NMR (75 MHz, METHANOL-d$_4$) d$_C$ ppm 122.2, 77.7, 65.8, 48.5, 48.2, 47.9, 47.6, 47.4, 47.1, 46.8, 41.8, 39.3, 31.9, 25.5, 25.0, 23.7; LC-MS (ESI), RT=1.60 min, m/z 352.3 [M+H]$^+$.

N$^2$-(3-(cyclohexyloxy)propyl)-N$^5$-(2-(methylamino)-2-oxoethyl)-1H-imidazole-2,5-dicarboxamide (MOC-15)

$^1$H NMR (300 MHz, METHANOL-d$_4$) d$_H$ ppm 7.76 (s, 1H), 3.86-4.19 (m, 2H), 3.41-3.70 (m, 4H), 2.78 (s, 3H), 1.83-2.03 (m, 4H), 1.44-1.83 (m, 5H), 1.17-1.44 (m, 5H), 0.97-1.17 (m, 1H); $^{13}$C NMR (75 MHz, METHANOL-d$_4$) d$_C$ ppm 77.6, 65.5, 48.5, 48.2, 47.9, 47.6, 47.4, 47.1, 46.8, 41.7, 36.9, 31.9, 29.5, 25.6, 25.0, 23.7; LC-MS (ESI), RT=1.59 min, m/z 366.4 [M+H]$^+$.

N$^5$-(2-(methylamino)-2-oxoethyl)-N$^2$-(2-phenoxyethyl)-1H-imidazole-2,5-dicarboxamide (MOC-16)

$^1$H NMR (300 MHz, METHANOL-d$_4$) d$_H$ ppm 7.63-7.83 (m, 1H), 7.13-7.43 (m, 2H), 6.79-7.13 (m, 3H), 4.11-4.30 (m, 2H), 4.03 (s, 2H), 3.80 (t, J=5.29 Hz, 2H), 2.77 (s, 3H), 1.42 (t, J=6.99 Hz, 1H); $^{13}$C NMR (75 MHz, METHANOL-d$_4$) d$_C$ ppm 129.1, 114.3, 48.5, 48.2, 47.9, 47.6, 47.3, 47.1, 46.8, 24.9; LC-MS (ESI), RT=1.40 min, m/z 346.3 [M+H]$^+$.

N$^5$-(2-(methylamino)-2-oxoethyl)-N$^2$-(3-phenoxypropyl)-1H-imidazole-2,5-dicarboxamide (MOC-17)

$^1$H NMR (300 MHz, METHANOL-d$_4$) d$_H$ ppm 7.65-7.88 (m, 1H), 7.16-7.37 (m, 2H), 6.79-7.05 (m, 3H), 3.91-4.22

(m, 4H), 3.61 (t, J=6.80 Hz, 2H), 2.77 (s, 3H), 2.11 (quin, J=6.33 Hz, 2H), 1.43 (t, J=6.99 Hz, 1H); $^{13}$C NMR (75 MHz, METHANOL-d$_4$) d$_C$ ppm 129.1, 120.4, 114.2, 65.3, 48.5, 48.2, 47.9, 47.6, 47.4, 47.1, 46.8, 41.8, 36.4, 29.0, 25.0; LC-MS (ESI), RT=1.39 min, m/z 360.4 [M+H]$^+$.

N$^2$-(4-isopropoxybutyl)-N$^5$-(2-(methylamino)-2-oxoethyl)-1H-imidazole-2,5-dicarboxamide (MOC-18)

$^1$H NMR (300 MHz, METHANOL-d$_4$) d$_H$ ppm 7.76 (s, 1H), 3.91-4.25 (m, 2H), 3.56-3.78 (m, 1H), 3.35-3.56 (m, 4H), 2.78 (s, 3H), 1.55-1.87 (m, 8H), 1.11-1.26 (m, 7H), 1.05 (t, J=6.61 Hz, 3H); $^{13}$C NMR (75 MHz, METHANOL-d$_4$) d$_C$ ppm 67.4, 48.5, 48.2, 47.9, 47.6, 47.4, 47.1, 46.8, 38.7, 27.1, 26.1, 25.0, 21.0; LC-MS (ESI), RT=1.79 min, m/z 340.4 [M+H]$^+$.

N$^5$-(2-(methylamino)-2-oxoethyl)-N$^2$-(6-methylheptyl)-1H-imidazole-2,5-dicarboxamide (MOC-19)

$^1$H NMR (300 MHz, METHANOL-d$_4$) d$_H$ ppm 7.77 (s, 1H), 4.04 (s, 2H), 2.78 (s, 3H), 1.63 (br. s., 1H), 1.25-1.55 (m, 9H), 0.76-1.11 (m, 7H); $^{13}$C NMR (75 MHz, METHANOL-d$_4$) δ ppm 48.5, 48.2, 47.9, 47.6, 47.4, 47.1, 46.8, 42.1, 39.5, 30.6, 28.6, 25.0, 23.8, 22.7, 13.0, 9.8; LC-MS (ESI), RT=2.66 min, m/z 338.4 [M+H]$^+$.

(E)-N$^2$-(3,7-dimethylocta-2,6-dien-1-yl)-N$^5$-(2-(methylamino)-2-oxoethyl)-1H-imidazole-2,5-dicarboxamide (MOC-20)

$^1$H NMR (300 MHz, METHANOL-d$_4$) d$_H$ ppm 7.76 (s, 1H), 5.31 (t, J=6.42 Hz, 1H), 5.12 (t, J=6.23 Hz, 1H), 3.86-4.17 (m, 4H), 2.78 (s, 3H), 1.94-2.24 (m, 4H), 1.76 (s, 3H), 1.62 (s, 3H), 1.67 (s, 3H); $^{13}$C NMR (75 MHz, METHANOL-d$_4$) d$_C$ ppm 123.7, 119.9, 48.5, 48.2, 47.9, 47.6, 47.4, 47.1, 46.8, 41.8, 39.3, 36.7, 26.1, 25.0, 24.5, 16.4, 15.0; LC-MS (ESI), RT=1.60 min, m/z 362.4 [M+H]$^+$.

N$^5$-(2-(methylamino)-2-oxoethyl)-N$^2$-(3-methylpentyl)-1H-imidazole-2,5-dicarboxamide (MOC-21)

$^1$H NMR (300 MHz, METHANOL-d$_4$) d$_H$ ppm 7.76 (s, 1H), 4.04 (s, 2H), 3.38-3.56 (m, 2H), 2.78 (s, 3H), 1.59-1.84 (m, 2H), 1.34-1.59 (m, 2H), 1.16-1.34 (m, 1H), 0.76-1.16 (m, 7H); $^{13}$C NMR (75 MHz, METHANOL-d$_4$) d$_C$ ppm 170.8, 122.1, 48.5, 48.2, 47.9, 47.6, 47.4, 47.1, 46.8, 41.8, 37.1, 35.9, 32.1, 29.1, 25.0, 18.0, 10.2; LC-MS (ESI), RT=1.39 min, m/z 310.4 [M+H]$^+$.

N$^2$-(2-acetamidoethyl)-N$^5$-(2-(methylamino)-2-oxoethyl)-1H-imidazole-2,5-dicarboxamide (MOC-22)

$^1$H NMR (300 MHz, METHANOL-d$_4$) d$_H$ ppm 7.76 (s, 1H), 4.04 (s, 1H), 3.35-3.65 (m, 3H), 2.78 (s, 2H), 1.88-2.07 (m, 3H), 1.66 (d, J=8.67 Hz, 2H), 1.04 (t, J=6.03 Hz, 1H); $^{13}$C NMR (75 MHz, METHANOL-d$_4$) d$_C$ ppm 48.5, 48.2, 47.9, 47.6, 47.4, 47.1, 46.8, 41.8, 39.1, 38.7, 25.0, 21.2; LC-MS (ESI), RT=2.82 min, m/z 311.33 [M+H]$^+$.

N$^5$-(4-guanidinobutyl)-N$^2$-(n-pentyl)-1H-imidazole-2,5-dicarboxamide (MOC-23)

$^1$H NMR (300 MHz, METHANOL-d$_4$) d$_H$ ppm 7.83 (s, 1H), 3.36-3.60 (m, 5H), 3.25 (br. s., 3H), 1.69 (br. s., 7H), 1.17-1.50 (m, 6H), 0.95 (br. s., 4H); $^{13}$C NMR (75 MHz, METHANOL-d$_4$) d$_C$ ppm 48.5, 48.3, 48.0, 47.7, 47.4, 47.1, 46.8, 40.8, 39.3, 28.9, 28.7, 25.9, 22.1, 13.0; LC-MS (ESI), RT=1.90 min, m z 338.4 [M+H]$^+$.

N$^5$-(4-guanidinobutyl)-N$^2$-(n-hexyl)-1H-imidazole-2,5-dicarboxamide (MOC-24)

$^1$H NMR (300 MHz, METHANOL-d$_4$) d$_H$ ppm 7.81 (br. s., 1H), 3.39-3.57 (m, 4H), 3.07-3.27 (m, 3H), 1.61-1.84 (m, 8H), 1.55 (t, J=7.16 Hz, 1H), 1.18-1.48 (m, 9H), 0.93 (br. s., 4H); $^{13}$C NMR (75 MHz, METHANOL-d$_4$) d$_C$ ppm 48.5, 48.2, 48.0, 47.7, 47.4, 47.1, 46.8, 40.8, 39.2, 31.3, 26.4, 25.9, 22.3, 13.0; LC-MS (ESI), RT=1.78 min, m/z 352.3 [M+H]$^+$.

N$^5$-(4-guanidinobutyl)-N$^2$-(n-heptyl)-1H-imidazole-2,5-dicarboxamide (MOC-25)

$^1$H NMR (300 MHz, METHANOL-d$_4$) d$_H$ ppm 7.90 (s, 1H), 3.35-3.57 (m, 5H), 3.25 (br. s., 2H), 1.60-1.86 (m, 7H), 1.34 (s, 6H), 1.39 (s, 4H), 0.79-1.03 (m, 4H); $^{13}$C NMR (75 MHz, METHANOL-d$_4$) d$_C$ ppm 48.6, 48.3, 48.0, 47.7, 47.4, 47.1, 46.9, 40.8, 39.6, 38.5, 31.6, 28.9, 28.7, 26.7, 26.3, 25.9, 22.3, 13.1; LC-MS (ESI), RT=1.78 min, m/z 366.4 [M+H]$^+$.

N$^2$-(2-(cyclohexyloxy)ethyl)-N$^5$-(4-guanidinobutyl)-1H-imidazole-2,5-dicarboxamide (MOC-26)

$^1$H NMR (300 MHz, METHANOL-d$_4$) d$_H$ ppm 7.76 (br. s., 1H), 3.50-3.75 (m, 7H), 3.44 (br. s., 3H), 3.25 (br. s., 3H), 1.81-2.09 (m, 5H), 1.63-1.81 (m, 9H), 1.45-1.63 (m, 2H), 1.11-1.44 (m, 7H); $^{13}$C NMR (75 MHz, METHANOL-d$_4$) d$_C$ ppm 77.5, 65.6, 48.5, 48.2, 47.9, 47.6, 47.4, 47.1, 46.8, 40.7, 37.0, 31.9, 25.8, 25.6, 23.7; LC-MS (ESI), RT=2.46 min, m/z 213.2 [M+H]$^+$.

N$^2$-(3-(cyclohexyloxy)propyl)-N$^5$-(4-guanidinobutyl)-1H-imidazole-2,5-dicarboxamide (MOC-27)

$^1$H NMR (300 MHz, METHANOL-d$_4$) d$_H$ ppm 7.73 (s, 1H), 3.38-3.76 (m, 7H), 3.13-3.30 (m, 3H), 1.79-2.07 (m, 5H), 1.63-1.79 (m, 7H), 1.56 (d, J=7.54 Hz, 1H), 1.12-1.42 (m, 5H); $^{13}$C NMR (75 MHz, METHANOL-d$_4$) d$_C$ ppm 77.5, 65.6, 48.5, 48.2, 47.9, 47.6, 47.4, 47.1, 46.8, 40.7, 37.0, 31.9, 25.8, 25.6, 23.7; LC-MS (ESI), RT=1.98 min, m/z 408.3 [M+H]$^+$.

N$^5$-(4-guanidinobutyl)-N$^2$-(2-phenoxyethyl)-1H-imidazole-2,5-dicarboxamide (MOC-28)

$^1$H NMR (300 MHz, METHANOL-d$_4$) d$_H$ ppm 8.01 (s, 1H), 7.28 (t, J=7.91 Hz, 2H), 6.82-7.10 (m, 3H), 4.19 (t, J=5.09 Hz, 2H), 3.84 (t, J=5.09 Hz, 2H), 3.44 (br. s., 2H), 3.25 (br. s., 2H), 1.69 (br. s., 5H); $^{13}$C NMR (75 MHz, METHANOL-d$_4$) d$_C$ ppm 129.2, 114.2, 48.5, 48.2, 47.9, 47.6, 47.4, 47.1, 46.8; LC-MS (ESI), RT=1.86 min, m/z 388.4 [M+H]$^+$.

N$^5$-(4-guanidinobutyl)-N$^2$-(3-phenoxypropyl)-1H-imidazole-2,5-dicarboxamide (MOC-29)

$^1$H NMR (300 MHz, METHANOL-d$_4$) d$_H$ ppm 7.73 (s, 1H), 7.13-7.38 (m, 2H), 6.80-7.05 (m, 3H), 4.10 (t, J=5.93 Hz, 2H), 3.61 (t, J=6.78 Hz, 2H), 3.44 (br. s., 2H), 3.14-3.30 (m, 2H), 2.11 (quin, J=6.36 Hz, 2H), 1.52-1.84 (m, 5H); $^{13}$C NMR (75 MHz, METHANOL-d$_4$) d$_C$ ppm 129.1, 120.4, 114.2, 65.3, 48.5, 48.2, 47.9, 47.6, 47.4, 47.1, 46.8, 40.8, 37.9, 36.4, 29.0, 26.6, 25.8; LC-MS (ESI), RT=1.51 min, m/z 402.3 [M+H]$^+$.

$N^5$-(4-guanidinobutyl)-$N^2$-(4-isopropoxybutyl)-1H-imidazole-2,5-dicarboxamide (MOC-30)

$^1$H NMR (300 MHz, METHANOL-d$_4$) d$_H$ ppm 7.73 (s, 1H), 3.35-3.74 (m, 8H), 3.14-3.28 (m, 2H), 1.69 (br. s., 9H), 1.16 (d, J=6.22 Hz, 6H); $^{13}$C NMR (75 MHz, METHANOL-d$_4$) d$_C$ ppm 71.5, 67.4, 48.5, 48.2, 47.9, 47.6, 47.4, 47.1, 46.8, 40.8, 38.7, 37.9, 27.1, 26.6, 26.1, 25.8, 21.0; LC-MS (ESI), RT=2.08 min, m/z 382.3 [M+H]$^+$.

$N^5$-(4-guanidinobutyl)-$N^2$-(6-methylheptyl)-1H-imidazole-2,5-dicarboxamide (MOC-31)

$^1$H NMR (300 MHz, METHANOL-d$_4$) d$_H$ ppm 7.74 (s, 1H), 3.38-3.57 (m, 2H), 3.14-3.30 (m, 2H), 1.54-1.83 (m, 6H), 1.22-1.54 (m, 9H), 0.81-1.09 (m, 7H); $^{13}$C NMR (75 MHz, METHANOL-d$_4$) d$_C$ ppm 48.5, 48.2, 47.9, 47.6, 47.3, 47.1, 46.8, 40.8, 39.5, 30.6, 28.6, 26.7, 25.8, 23.8, 22.7, 13.0, 9.8; LC-MS (ESI), RT=1.19 min, m z 380.3 [M+H]$^+$.

$N^5$-(4-guanidinobutyl)-$N^2$-(3-methylpentyl)-1H-imidazole-2,5-dicarboxamide (MOC-32)

$^1$H NMR (300 MHz, METHANOL-d$_4$) d$_H$ ppm 7.73 (s, 1H), 3.35-3.58 (m, 4H), 3.14-3.30 (m, 2H), 1.69 (br. s., 6H), 1.35-1.59 (m, 3H), 1.24 (td, J=7.06, 13.75 Hz, 1H), 0.77-1.09 (m, 6H); $^{13}$C NMR (75 MHz, METHANOL-d$_4$) d$_C$ ppm 48.5, 48.2, 47.9, 47.6, 47.4, 47.1, 46.8, 40.8, 37.1, 35.9, 32.1, 29.1, 26.6, 25.8, 18.0, 10.2; LC-MS (ESI), RT=1.79 min, m/z 352.3 [M+H]$^+$.

$N^2$-(n-hexyl)-$N^5$-(pyridin-2-ylmethyl)-1H-imidazole-2,5-dicarboxamide (MOC-33)

$^1$H NMR (300 MHz, METHANOL-d$_4$) d$_H$ ppm 8.52 (d, J=4.53 Hz, 1H), 7.70-7.93 (m, 2H), 7.45 (d, J=7.93 Hz, 1H), 7.19-7.40 (m, 1H), 4.71 (s, 2H), 3.39 (t, J=6.99 Hz, 2H), 1.51-1.76 (m, 2H), 1.37 (br. s., 6H), 0.93 (t, J=6.42 Hz, 3H); $^{13}$C NMR (75 MHz, METHANOL-d$_4$) d$_C$ ppm 158.6, 157.8, 148.5, 137.5, 122.5, 121.9, 121.6, 48.5, 48.2, 47.9, 47.7, 47.4, 47.1, 46.8, 43.7, 39.0, 31.3, 29.2, 26.3, 22.3; LC-MS (ESI), RT=2.74 min, m/z 330.3 [M+H]$^+$.

$N^2$-(2-acetamidoethyl)-$N^5$-(pyridin-2-ylmethyl)-1H-imidazole-2,5-dicarboxamide (MOC-34)

$^1$H NMR (300 MHz, METHANOL-d$_4$) d$_H$ ppm 8.65 (d, J=4.91 Hz, 1H), 8.08-8.32 (m, 1H), 7.69-7.93 (m, 2H), 7.54-7.69 (m, 1H), 3.47 (dd, J=5.85, 19.83 Hz, 4H), 1.97 (s, 3H), 0.92-1.19 (m, 1H); $^{13}$C NMR (75 MHz, METHANOL-d$_4$) d$_C$ ppm 142.1, 124.0, 123.6, 48.5, 48.2, 47.9, 47.7, 47.4, 47.1, 46.8, 39.3, 38.7, 21.2; LC-MS (ESI), RT=3.18 min, m/z 331.3 [M+H]$^+$.

$N^5$-(furan-2-ylmethyl)-$N^2$-(n-hexyl)-1H-imidazole-2,5-dicarboxamide (MOC-35)

$^1$H NMR (300 MHz, METHANOL-d$_4$) d$_H$ ppm 7.75 (s, 1H), 7.45 (s, 1H), 6.18-6.55 (m, 2H), 4.57 (s, 2H), 3.36-3.42 (m, 2H), 1.61 (d, J=7.18 Hz, 2H), 1.37 (br. s., 7H), 0.76-1.06 (m, 3H); $^{13}$C NMR (75 MHz, METHANOL-d$_4$) d$_C$ ppm 158.6, 151.7, 142.0, 121.8, 110.0, 106.8, 48.5, 48.2, 47.9, 47.7, 47.4, 47.1, 46.8, 38.9, 35.4, 31.3, 29.2, 26.3, 22.3, 13.0; LC-MS (ESI), RT=2.43 min, m/z 319.3 [M+H]$^+$.

$N^2$-(2-acetamidoethyl)-$N^5$-(furan-2-ylmethyl)-1H-imidazole-2,5-dicarboxamide (MOC-36)

$^1$H NMR (300 MHz, METHANOL-d$_4$) d$_H$ ppm 7.75 (s, 1H), 7.45 (s, 1H), 6.32 (s, 1H), 6.37 (s, 1H), 4.57 (s, 2H), 3.35-3.65 (m, 5H), 1.96 (s, 3H); $^{13}$C NMR (75 MHz, METHANOL-d$_4$) d$_C$ ppm 172.6, 159.0, 151.8, 142.0, 110.0, 106.8, 48.5, 48.2, 47.9, 47.7, 47.4, 47.1, 46.8, 39.0, 38.7, 35.4, 21.2; LC-MS (ESI), RT=1.71 min, m/z 319.13 [M+H]$^+$.

Example 8

Biological Screening: General

All reagents used in the biological screenings were purchased from Sigma-Aldrich (UK) of molecular biology grade unless stated otherwise.

Example 9

NS3 Protein
(i) NS3 Constructs

A synthetic gene coding for the HCV NS3 domain of genotype 4a, the most abundant HCV in Saudi Arabia and Egypt [Massariol, M.-J.; Zhao, S.; Marquis, M.; Thibeault, D.; White, P. W., Protease and helicase activities of hepatitis C virus genotype 4, 5, and 6 NS3-NS4A proteins. *Biochemical and Biophysical Research Communications* 2010, 391 (1), 692-697], was synthesized by GenScript (Hong Kong), the nucleotide sequence was optimized for *E. coli* codon usage. The synthetic gene was cloned as NdeI-BamHI fragment into the expression vector pET-3a Novagen®. The obtained construct was sequenced to confirm that we had the right clone and the gene was in the correct frame.
(ii) NS3 Protein Information
Accession GU085486.1
HCV genotype 4a (The most common genotype in Saudi Arabia) [Bawazir, A.; AlGusheri, F.; Jradi, H.; AlBalwi, M.; Abdel-Gader, A.-G., Hepatitis C virus genotypes in Saudi Arabia: a future prediction and laboratory profile. *Virology journal* 2017, 14 (1), 208-208]
NS3 from 4 to 182 aa (L/E, F/E, I/Q, V/E, L/Q, C/S)
NS4A 632 to 685 aa (i/n)
G svvivgrvnl sgdtayaqqt rgeestqets qtgrdtnenc gevqvlstat qsflgtavng vmwtvyhgag sktisgpkgp vnqmytnvdq dlvgwpsppg vksltpctcg asdlylvtrh advvpvrrrg dtrgallspr pistlk- gssg gpllcpmgha aglfraavst rgvakavdfv pveslett mrsp
NS4A/NS3 Fusion protein expression in pET-28a
NS3 protease domain 1-181 aa+N-terminal T7 tag and C-terminal His tag
M ASMTGGQQMG apitayaqqt rglfstivts ltgrdtnenc gevqvlstat qsflgtavng vmwtvyhgag sktisgpkgp vnqmytnvdq dlvgwpsppg vksltpctcg asdlylvtrh advvpvrrrg dtrgallspr pistlkgssg gpllcpmgha aglfraavct rgvakavdfv pveslettmr sGSHHHHHH
Expression in pET-3a
(iii) Protein eNS4A Expression The sequence of NS3 domain for genotype 4a, was expressed in *E. coli* Rosette (DE3) pLysS according to standard protocol [Kim, J.; Morgenstern, K.; Lin, C.; Fox, T.; Dwyer, M.; Landro, J.; Chambers, S.; Markland, W.; Lepre, C.; O'malley, E., Crystal structure of the hepatitis C virus NS3 protease domain complexed with a synthetic NS4A cofactor peptide. *Cell* 1996, 87 (2), 343-355]. Therefore, a synthetic gene for NS3 domain was subcloned in the expression vector pET-3a. In the process, a 100 mL of bacterial culture in Luria Broth medium was grown overnight at 37° C. and used for inoculation of 10 L LB in a 14-liter fermenter flask (New Brunswick Scientific Co., CT, USA). The media was supplemented with 50 µg/mL ampicillin. The culture grew until the $OD_{600}$ reached 0.5-0.6, then it was cooled to 25° C. and 1 mM IPTG was added. Expression was followed overnight, and then cells were harvested.

(iv) Protein Purification

Figure 4:
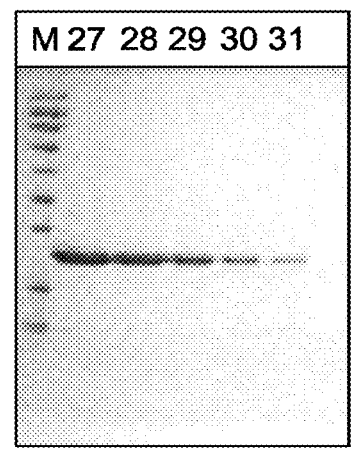
FIG. 4 shows the purity of NS3 using SDS-Page electrophoresis method.

The produced protein was purified using equilibrated Ni-NTA beads and the poly-histidine tag was not removed. In the process, cells were re-suspended (1 g/5 mL) in buffer (50 mM HEPES, 0.3 M NaCl, 10% glycerol, 2 mM β-mercaptoethanol, pH 8). Lysozymes were added (1 mg/mL) followed by protease inhibitor cocktail tablet and the suspension was sonicated. Cell lysate was centrifuged to collect the clear supernatant that contained the desired NS3 protein. The protein was purified using pre-equilibrated Ni-NTA beads (Qiagen, USA). Beads were washed with buffer (50 mM HEPES, 0.3 M NaCl, 10% glycerol, 2 mM β-mercaptoethanol, 20 mM imidazole, pH 8) and eluted with another buffer (50 mM HEPES, 0.3 M NaCl, 10% glycerol, 2 mM β-mercaptoethanol, 350 mM imidazole, pH 8). Fractions were collected and concentrated using Amicon Ultra-4 3000 MWCO centrifugal device (Millipore, Germany). Protein purity after Ni-affinity purification step was not less than 70%. The purity, as estimated by SDS-PAGE, was sufficient to perform all investigations of this study and the protein was stable for several hours at test conditions (see FIG. 4) [Massariol, M.-J.; Zhao, S.; Marquis, M.; Thibeault, D.; White, P. W., Protease and helicase activities of hepatitis C virus genotype 4, 5, and 6 NS3-NS4A proteins. *Biochemical and Biophysical Research Communications* 2010, 391 (1), 692-697]. The concentration of NS3 in the final concentrate was measured using Nanodrop™ nanoscale spectrophotometer.

When needed, further purification of the protein was accomplished on Superdex 75 16/90 column (GE Healthcare, USA) equilibrated in 20 mM HEPES, 10 mM DDT, 200 mM NaCl, pH 7.6 run at rate of 1 mL/min followed by SDS-PAGE for purity estimation.

Example 10

NS4A

The cofactor NS4A and the fluorescent fluorescein isothiocyanate NS4A (FITC-NS4A) were purchased from GenScript (Hong Kong). NS4A structure was identical to that of HCV genotype 4a with two lysine residues added at both the N- and C-termini. Thus the structure of NS4A used in this study was LL-$G_{21}$SVVIVGRIVLSG$_{33}$-LL.

Example 11

Binding and Competition Assay

Binding buffer (20 mM HEPES, 10 mM DTT, 200 mM NaCl, pH 7.6), a mixture of NS3 (1.8 µM) and FITC-NS4A (0.1 M) at the calculated affinity constant concentration were placed in a 96-well plate as binding test solution. A serial dilution of MOC compounds (dissolved in 1.5% DMSO in binding buffer) (1/2 dilution starting from 150 µM to 0.292 µM) was mixed gently with the binding text solution for 60 minutes in the dark. The dissociation constant was calculated according to the recommended equation embedded in GraphPad Prism v8.

Example 12

Enzyme Inhibition Assay

The assay was performed using SensoLyte-520® HCV protease assay kit Fluorometric® (Anaspec, Fremont, Calif., USA) according to a modified procedure to suit the purpose of determination of allosteric inhibition. NS3 (4.0 µM) was mixed with MOC-23 (6.3 µM) for 15 minutes. Afterwards, 5-FAM/QXL™520 fluorescence resonance energy transfer (FRET) peptide was added as instructed by the assay kit manual. The sequence of this FRET peptide (5-FAM-SLGRKIQIQ) is derived from the cleavage site of NS4A/NS4B. In the FRET peptide, the fluorescence of 5-FAM is quenched by QXL™520. Upon cleavage into two separate fragments by HCV NS3/4A protease, the fluorescence of 5-FAM is recovered, and can be monitored at 490 nm/520 nm (excitation/emission). Controls included buffer, compound, compound+NS3, NS3+NS4A and FRET peptide separately. All test wells and controls were repeated in triplicates at the same 96-well plate.

Example 13

Biological Screening Results

The binding affinity test was performed using fluorescence anisotropy technique. In this test, maximum fluorescence was first determined at optimal ratio of NS3 (1.8 µM) and FITC-NS4A (0.1 µM). Compounds that compete with NS4A should be able to decrease the fluorescence of this mixture because they prevent the binding to occur and it should be concentration-dependent. Results showed some compounds suppressed the fluorescence emitted upon binding of NS4A with NS3. However, we found that MOC-23 showed highest affinity and more reproducible results than other compounds (see FIG. 5). It could effectively compete with FITC-NS4A at dissociation constant $K_d$=6.303±0.3 µM). The reproducibility was checked using another batch of the express NS3 protein following the same procedure and the value was calculated=7.815±1.014 µM. Compound MOC-24 showed binding affinity at similar level but results were less reproducible and standard error was higher. Therefore, compound MOC-23 was tested for its ability to inhibit the NS3 enzyme. MOC-23 at its binding affinity concentration (6.3 µM) was able to inhibit NS3 and abolished any proteolytic activity of the enzyme (see FIG. 6).

The invention claimed is:
1. A composition, comprising:
non-structural protein 3 (NS3), and
a compound of formula (I)

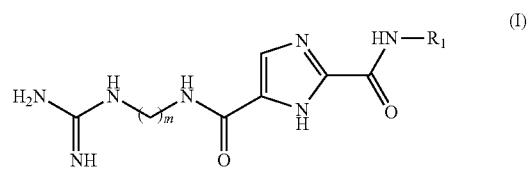

a salt thereof, a solvate thereof, or a mixture thereof,
wherein:
$R_1$ is n-pentyl; and
m is 4,
wherein the compound of formula (I) is bonded to an active site of the NS3 to inhibit protease activity of the NS3.

2. The composition of claim 1, further comprising:
a pharmaceutically acceptable carrier and/or excipient.

3. The composition of claim 2, wherein the pharmaceutically acceptable carrier and/or excipient is at least one selected from the group consisting of a buffer, an inorganic salt, a fatty acid, a vegetable oil, a synthetic fatty ester, a surfactant, and a polymer.

4. The composition of claim 2, further comprising an antiviral agent.

5. The composition of claim 2, further comprising a body fluid.

\* \* \* \* \*